(12) United States Patent
Sakurai et al.

(10) Patent No.: US 11,499,931 B2
(45) Date of Patent: Nov. 15, 2022

(54) SENSOR

(71) Applicant: NABTESCO CORPORATION, Tokyo (JP)

(72) Inventors: Kazuhiko Sakurai, Tokyo (JP); Masaki Harada, Tokyo (JP); Koki Akai, Tokyo (JP); Shuichi Kamagata, Tokyo (JP)

(73) Assignee: NABTESCO CORPORATION, Tokyo (JP)

(*) Notice: Subject to any disclaimer, the term of this patent is extended or adjusted under 35 U.S.C. 154(b) by 238 days.

(21) Appl. No.: 16/829,754

(22) Filed: Mar. 25, 2020

(65) Prior Publication Data
US 2020/0340936 A1   Oct. 29, 2020

(30) Foreign Application Priority Data

Apr. 26, 2019 (JP) .............................. JP2019-085668
Nov. 5, 2019 (JP) .............................. JP2019-200720

(51) Int. Cl.
*G01N 27/07* (2006.01)
*G01N 33/28* (2006.01)

(52) U.S. Cl.
CPC ......... *G01N 27/07* (2013.01); *G01N 33/2888* (2013.01)

(58) Field of Classification Search
CPC . G01N 27/07; G01N 33/2858; G01N 33/2888
USPC ....................................................... 324/693
See application file for complete search history.

(56) References Cited

U.S. PATENT DOCUMENTS

| | | | | | |
|---|---|---|---|---|---|
| 5,179,346 | A | * | 1/1993 | McGee | G01N 15/0656 |
| | | | | | 324/693 |
| 5,402,113 | A | * | 3/1995 | Naas | G01N 33/2858 |
| | | | | | 324/698 |
| 7,112,973 | B2 | * | 9/2006 | Itomi | G01N 33/2888 |
| | | | | | 73/61.42 |

(Continued)

FOREIGN PATENT DOCUMENTS

| | | | | |
|---|---|---|---|---|
| CN | 111855755 | A * | 10/2020 | ............. G01N 27/07 |
| CN | 112782237 | A * | 5/2021 | ........... B25J 19/0062 |

(Continued)

OTHER PUBLICATIONS

Extended European Search Report dated Dec. 9, 2020 issued in corresponding European Patent Application No. 20165531.3 (13 pgs.).

*Primary Examiner* — Jermele M Hollington
*Assistant Examiner* — Sean Curtis
(74) *Attorney, Agent, or Firm* — Pillsbury Winthrop Shaw Pittman, LLP

(57) ABSTRACT

A sensor relating to one embodiment of the present invention includes a first electrode, a second electrode, an attracting portion arranged between the first electrode and the second electrode, where the attracting portion attracts conductive particles smaller than a gap between the first electrode and the second electrode to cause a change in electrical resistance between the first electrode and the second electrode, and a short circuit preventing portion for preventing a large-diameter conductive piece from causing a short circuit between the first electrode and the second electrode, where the large-diameter conductive piece has a larger dimension than the gap between the first electrode and the second electrode.

5 Claims, 12 Drawing Sheets

(56) References Cited

U.S. PATENT DOCUMENTS

| | | | | |
|---|---|---|---|---|
| 7,151,383 | B2 * | 12/2006 | Itomi | G01N 33/2888 |
| | | | | 73/61.42 |
| 8,058,871 | B2 * | 11/2011 | Guo | G01R 33/098 |
| | | | | 324/244 |
| 10,317,354 | B2 * | 6/2019 | Ricci | F16N 29/04 |
| 10,359,077 | B2 * | 7/2019 | Ito | F16C 19/383 |
| 10,705,038 | B2 * | 7/2020 | Ricci | F16N 29/04 |
| 10,705,039 | B2 * | 7/2020 | Kiriyama | G01N 27/12 |
| 11,249,041 | B2 * | 2/2022 | Amamiya | G01N 27/226 |
| 11,346,871 | B2 * | 5/2022 | Harada | F16N 9/00 |
| 2005/0212533 | A1 * | 9/2005 | Itomi | G01N 33/2888 |
| | | | | 324/698 |
| 2006/0125487 | A1 * | 6/2006 | Itomi | G01N 33/2888 |
| | | | | 324/533 |
| 2009/0314064 | A1 * | 12/2009 | Augros | F01M 11/10 |
| | | | | 73/61.42 |
| 2018/0031504 | A1 * | 2/2018 | Ricci | G01N 27/06 |
| 2018/0223907 | A1 * | 8/2018 | Ito | F16C 33/667 |
| 2018/0275083 | A1 * | 9/2018 | Kiriyama | G01N 27/12 |
| 2019/0154608 | A1 * | 5/2019 | Nakamura | G01N 33/2858 |
| 2019/0257777 | A1 * | 8/2019 | Ricci | F16N 29/04 |
| 2020/0057044 | A1 * | 2/2020 | Nakamura | G01N 27/06 |
| 2020/0340936 | A1 * | 10/2020 | Sakurai | G01N 15/0656 |
| 2021/0132126 | A1 * | 5/2021 | Harada | G01R 27/16 |
| 2021/0148847 | A1 * | 5/2021 | Amamiya | A47J 37/1266 |
| 2021/0181177 | A1 * | 6/2021 | Sakurai | G01N 15/0606 |
| 2021/0263009 | A1 * | 8/2021 | Shenouda | G01N 15/1031 |

FOREIGN PATENT DOCUMENTS

| | | | | |
|---|---|---|---|---|
| CN | 112986337 A * | 6/2021 | | G01N 15/0606 |
| DE | 102006047927 A1 | 4/2008 | | |
| DE | 102016220835 A1 | 4/2018 | | |
| DE | 112016003543 T5 | 4/2018 | | |
| DE | 102018204674 A1 * | 9/2018 | | G01N 27/12 |
| DE | 102018219895 A1 * | 5/2019 | | F16H 55/02 |
| DE | 102018219625 A1 * | 5/2020 | | G01N 15/0606 |
| DE | 102020205944 A1 * | 11/2021 | | |
| EP | 3742162 A2 * | 11/2020 | | G01N 27/07 |
| EP | 3783348 A1 * | 2/2021 | | A47J 37/1266 |
| EP | 3819635 A1 * | 5/2021 | | B25J 19/0062 |
| EP | 3839504 A2 * | 6/2021 | | G01N 15/0606 |
| EP | 3961201 A1 * | 3/2022 | | G01N 27/04 |
| FR | 2927401 A1 * | 8/2009 | | B03C 1/282 |
| JP | 2002-286697 A | 10/2002 | | |
| JP | 2002286697 A * | 10/2002 | | |
| JP | 2005331324 A * | 12/2005 | | |
| JP | 2005337938 A * | 12/2005 | | |
| JP | 2005337945 A * | 12/2005 | | |
| JP | 2005337981 A * | 12/2005 | | |
| JP | 2006170667 A * | 6/2006 | | G01N 33/2888 |
| JP | 2006300606 A * | 11/2006 | | |
| JP | 2006300608 A * | 11/2006 | | |
| JP | 4643243 B2 * | 3/2011 | | G01N 33/2888 |
| JP | 4711723 B2 * | 6/2011 | | |
| JP | 2017-190813 A | 10/2017 | | |
| JP | 2019128311 A * | 8/2019 | | |
| JP | 2020183932 A * | 11/2020 | | G01N 27/07 |
| JP | 2021057188 A * | 4/2021 | | |
| JP | 2021076386 A * | 5/2021 | | B25J 19/0062 |
| JP | 2021096168 A * | 6/2021 | | G01N 15/0606 |
| KR | 20210077590 A * | 10/2020 | | |
| KR | 20210054446 A * | 5/2021 | | G01N 27/07 |
| KR | 20210077590 A * | 5/2021 | | G01N 27/07 |
| KR | 20220005467 A * | 1/2022 | | G01N 27/07 |
| WO | WO-2010150688 A1 * | 12/2010 | | G01N 33/2888 |
| WO | WO-2020004273 A1 * | 1/2020 | | B32B 7/025 |
| WO | WO-2020217508 A1 * | 10/2020 | | G01N 27/04 |

\* cited by examiner

SENSOR

CROSS-REFERENCE TO RELATED APPLICATIONS

This application is based on and claims the benefit of priority from Japanese Patent Application Serial Nos. 2019-085668 (filed on Apr. 26, 2019) and 2019-200720 (filed on Nov. 5, 2019), the contents of which are incorporated herein.

TECHNICAL FIELD

The present invention relates to a sensor.

BACKGROUND

A mechanical device such as a speed reducer is housed in a housing filled with a lubricating oil in order to prevent the mechanical parts such as gears from being damaged. If the mechanical parts are worn out during operation of the mechanical device, abrasion powder (for example, a conductive substance such as iron powder) is mixed into the lubricating oil. The abrasion powder is, for example, of a conductive substance such as iron powder. As the mechanical parts are increasingly worn out and enter a wear-out failure period, which is defined in a failure rate curve (a bathtub curve), an increased amount of abrasion powder is mixed into the lubricating oil. For this reason, a sensor for sensing the amount of the abrasion powder in the lubricating oil allows for accurate preventive maintenance of the mechanical parts.

For example, Japanese Patent Application Publication No. 2002-286697 discloses an oil check sensor, which can be used for the above purposes. The disclosed oil check sensor is mounted to, for example, a transmission of an automobile and configured to check, for example, deterioration of an oil in an oil container and the degree of wear of mechanical parts lubricated with the oil. This sensor includes a pair of electrodes and a magnet for attracting iron powder or the like (a conductive substance) contained in the oil. Based on the resistance between the electrodes, which depends on the conductive substance attracted, the sensor senses the amount of the conductive substance in the oil.

The abrasion powder to be detected in the speed reducer or the like first increases due to initial wear, then remains substantially constant during normal operation and finally suddenly increases before occurrence of failures. The sensor may be configured to sense the increase in the amount of the abrasion powder before the occurrence of failures, but may malfunction when a large amount of abrasion powder is produced due to initial wear, for example, when the speed reducer has a large size. If such is the case, the sensor may not be capable of sensing the increase in the amount of the abrasion powder before the occurrence of failures, which is originally intended to be sensed. There is also a demand for prevention of sensor malfunction and thereby detection of failures in advance in order to reliably suspend and replace the speed reducer and the like.

Furthermore, while the mechanical device such as a speed reducer is manufactured, foreign matter having a large particle size (for example, a cutting chip or the like) generated by cutting or other methods of processing may adhere to the constituent components of the mechanical device and get mixed in with the lubricating oil. If such foreign matter having a large particle size adheres to the sensor, a short circuit occurs between the paired electrodes even with little abrasion powder produced. For the reasons stated above, the sensor for sensing the amount of abrasion powder may operate unexpectedly even when a small amount of abrasion powder is produced.

SUMMARY

The present invention is made in light of the above, and aims to achieve an object of providing a sensor that can be prevented from operating unexpectedly due to foreign matter mixed in and a difference found between the amount of abrasion powder produced and the designated amount to trigger the operation.

A first aspect of the present invention provides a sensor including a first electrode, a second electrode, an attracting portion arranged between the first electrode and the second electrode, where the attracting portion attracts conductive particles smaller than a gap between the first electrode and the second electrode to cause a change in electrical resistance between the first electrode and the second electrode, and a short circuit preventing portion for preventing a large-diameter conductive piece from causing a short circuit between the first electrode and the second electrode, where the large-diameter conductive piece has a larger dimension than the gap between the first electrode and the second electrode. In this way, the above-described problem is solved.

The sensor includes a short circuit preventing portion for preventing a large-diameter conductive piece (i.e., foreign matter) from causing a short circuit between the first electrode and the second electrode, and the large-diameter conductive piece has a larger dimension than the gap between the first electrode and the second electrode. This can prevent a short circuit from being caused by a large-diameter conductive piece between the first electrode and the second electrode. As a result, the sensor can be prevented from operating unexpectedly.

The sensor relating to the first aspect of the present invention can include a sensing unit for sensing the change in electrical resistance between the first electrode and the second electrode.

In the sensor relating to the first aspect of the present invention, the short circuit preventing portion can be a protrusion having an insulation property, and the protrusion is provided on at least one of the first electrode and the second electrode. With such configurations, even if a large-diameter conductive piece is attracted, the protrusion can prevent electrical contact between the large-diameter conductive piece and at least one of the first and second electrodes. Accordingly, a short circuit can be prevented from being caused by the large-diameter conductive piece between the first electrode and the second electrode, which can prevent the sensor from operating unexpectedly.

In the sensor relating to the first aspect of the present invention, the short circuit preventing portion can be a protrusion provided on the attracting portion. Since the protrusion is provided between the first electrode and the second electrode as described above, a large-diameter conductive piece may be attracted but can be prevented from electrically contacting at least one of the first electrode and the second electrode. Accordingly, a short circuit can be prevented from being caused by the large-diameter conductive piece between the first electrode and the second electrode, which can prevent the sensor from operating unexpectedly.

In the sensor relating to the first aspect of the present invention, the short circuit preventing portion and the attracting portion may form a one-piece structure.

In the sensor relating to the first aspect of the present invention, the short circuit preventing portion and the attracting portion may be separate members.

In the sensor relating to the first aspect of the present invention, the short circuit preventing portion can have an insulation property.

In the sensor relating to the first aspect of the present invention, the short circuit preventing portion can be a wire extending along a direction intersecting with a direction in which the first electrode and the second electrode face each other. With this configuration, even if a large-diameter conductive piece is attracted, the wire can prevent the large-diameter conductive piece from electrically contacting at least one of the first and second electrodes. Accordingly, a short circuit can be prevented from being caused by the large-diameter conductive piece between the first electrode and the second electrode, which can prevent the sensor from operating unexpectedly.

A sensor relating to a second aspect of the present invention includes a plurality of detecting units each including a pair of electrodes and an attracting portion arranged between the paired electrodes, where the attracting portion attracts conductive particles to cause a change in electrical resistance between the paired electrodes, and a sensing unit for outputting a signal when a designated number of the detecting units experience a change in electrical resistance. In this way, the above-described problem is solved.

The sensor includes the plurality of detecting units, and the sensing unit outputs a signal when a designated number of the detecting units experience a drop in electrical resistance. In this way, the sensing unit can be configured such that no signal is output when just one of the detecting units experiences a change in electrical resistance caused by a large-diameter conductive piece. Accordingly, the sensor can be prevented from operating unexpectedly due to a large-diameter conductive piece.

In the sensor relating to the second aspect of the present invention, while no conductive particles are attracted, the detecting units exhibit the same electrical resistance. With this configuration, the same voltage can be applied to the detecting units, which can lower the voltage to be applied to the sensor.

In the sensor relating to the second aspect of the present invention, the detecting units can be connected in parallel to each other. With this configuration, when compared with a case where the detecting units are connected in series, the voltage applied between the paired electrodes in each detecting unit can be lowered.

A third aspect of the present invention provides a sensor including a first electrode, a second electrode, an attracting portion arranged between the first electrode and the second electrode, where the attracting portion attracts conductive particles to cause a change in electrical resistance between the first electrode and the second electrode, a sensing unit for sensing that a predetermined amount of the conductive particles is attracted, and a sensitivity adjusting unit for adjusting the attraction of the conductive particles to change sensitivity. In this way, the above-described problem is solved.

In the sensor relating to the third aspect of the present invention, the sensitivity adjusting unit adjusts the attraction of the conductive particles. With this configuration, even when a large amount of abrasion powder is attracted, the sensitivity of the sensor can be adjusted depending on the attraction of the conductive particles, so that the sensing can be reliably performed. In particular, when the sensor is placed in a large-size speed reducer or the like and a large amount of abrasion powder is thus produced during the initial stage, the sensor can be configured such that the attraction of the initial abrasion powder is limited or the sensing scheme is changed if a large amount of abrasion powder is attracted. This enables the sensor to reliably perform the sensing.

In the sensor relating to the third aspect of the present invention, the sensitivity adjusting unit can adjust the distance between the first electrode and the second electrode.

In the sensor relating to the third aspect of the present invention, the sensitivity adjusting unit can be a group of insulating walls with different heights and one of the insulating walls is arranged between the first electrode and the second electrode.

In the sensor relating to the third aspect of the present invention, the sensitivity adjusting unit can be a group of insulators with different thicknesses between the first electrode and the second electrode, and one of the insulators is arranged between the first electrode and the second electrode.

In the sensor relating to the third aspect of the present invention, an end of the first electrode can be flush with the second electrode.

In the sensor relating to the third aspect of the present invention, the sensitivity adjusting unit can be at least a further attracting portion for attracting the conductive particles provided separately from the attracting portion.

In the sensor relating to the third aspect of the present invention, the sensitivity adjusting unit can include a surface treatment layer for the first electrode and the second electrode.

A fourth aspect of the present invention provides a sensor including an outer electrode shaped like a tube, where the outer electrode has a bottom portion, an insulator arranged in the outer electrode, where the insulator is a bottomed internal tube, a magnet arranged within the insulator, an inner electrode arranged within the insulator, where the inner electrode is closer to an opening of the outer electrode in an axial direction than the magnet is, a sensing unit for sensing that the magnet attracts a predetermined amount of conductive particles to such an extent that a short-circuit occurs between the outer electrode and the inner electrode, and a sensitivity adjusting unit for adjusting the attraction of the conductive particles to change sensitivity. In this way, the above-described problem is solved.

In the sensor relating to the fourth aspect of the present invention, the sensitivity adjusting unit adjusts attraction of conductive particles. With this configuration, even when a large amount of abrasion powder is attracted, the sensitivity of the sensor can be adjusted depending on the attraction of the conductive particles, so that the sensing can be reliably performed. In particular, when the sensor is placed in a large-size speed reducer or the like and a large amount of abrasion powder is thus produced during the initial stage, the sensor can be configured such that the attraction of the initial abrasion powder is limited or the sensing scheme is changed if a large amount of abrasion powder is attracted. This enables the sensor to reliably perform the sensing.

In the sensor relating to the fourth aspect of the present invention, the insulator can have a tubular portion and a sheet-shaped bottom portion.

The sensor relating to the fourth aspect of the present invention may include a fastening portion extending in the axial direction through the inner electrode, the magnet, the bottom portion of the insulator and the bottom portion of the outer electrode.

Advantageous Effects

The above-described aspects of the present invention can produce an effect of providing a sensor that can be prevented from operating unexpectedly and thus achieve improved reliability.

DESCRIPTION OF THE EMBODIMENTS

The following describes a sensor relating to a first embodiment of the present invention with reference to the drawings. The constituents common to more than one drawing are denoted by the same reference signs throughout the drawings. It should be noted that the drawings do not necessarily appear to an accurate scale for the sake of convenience of explanation.

Figure 1:
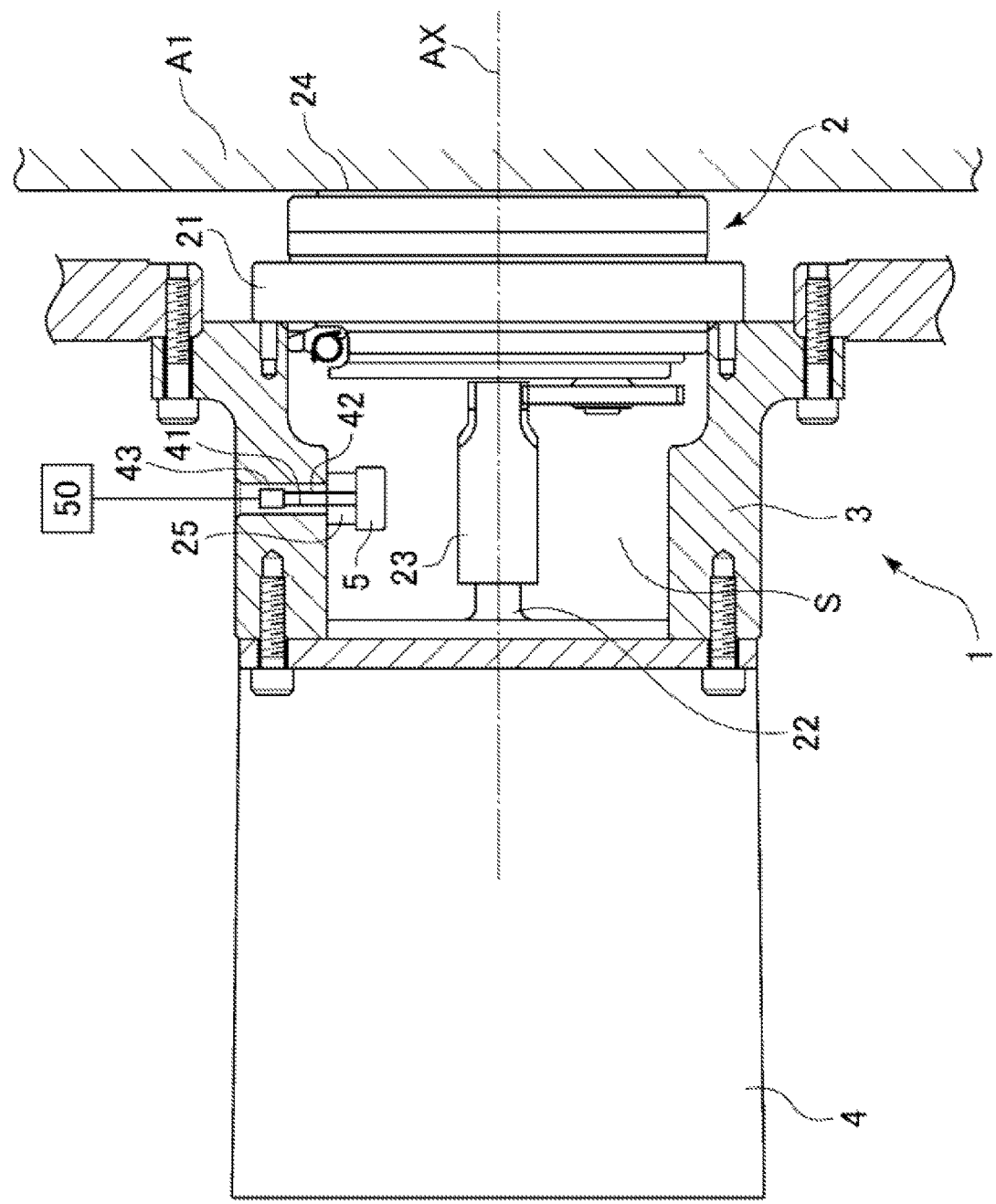
FIG. 1 is a sectional view showing one example of a mechanical device including a sensor relating to a first embodiment of the present invention.

FIG. 1 is a sectional view showing one example of a mechanism 1 including a sensor 5 relating to one embodiment of the present invention. The mechanism 1 is, for example, a movable part such as a robot arm. The mechanism 1 includes a speed reducer 2, a flange 3 provided on the input side, a servomotor 4, and a device A1 provided on the output side.

The speed reducer 2 includes a casing 21 mounted to the flange 3, an input shaft 23 connected to an output shaft 22 of the servomotor 4, and an output shaft 24 connected to the output-side device A1. The input shaft 23 and the output shaft 24 are supported to be capable of rotating about an axis AX relative to the casing 21. The output from the servomotor 4 is input to the speed reducer 2 via the input shaft 23, reduced by the speed reducer 2, and then transmitted to the output-side device A1 via the output shaft 24. Thus, the output-side device A1 and the flange 3 are capable of rotating relative to each other.

The flange 3 is a tubular member and houses therein at least a portion of the speed reducer 2. The servomotor 4 is mounted to the flange 3. An opening at one end of the flange 3 in the direction along the axis AX is closed by the speed reducer 2, and an opening at the other end of the flange 3 is closed by the servomotor 4. Thus, the flange 3 has a tightly closed hollow portion (a space S) formed therein. The space S contains therein a lubricating oil, so that the flange 3 also serves as an oil bath.

The casing 21 of the speed reducer 2 houses therein a gear mechanism, for example. The space within the casing 21 communicates with the space S within the flange 3. As the speed reducer 2 operates, the gear mechanism in the casing 21 rotates, which subsequently causes the lubricating oil to circulate between the space in the casing 21 and the space S in the flange 3. As the lubricating oil circulates, a conductive substance such as abrasion powder (conductive abrasion powder) produced in the speed reducer 2 moves into the space S in the flange 3.

In the space S, a sensor 5 is installed for sensing the amount of the conductive substance contained in the lubricating oil. The sensor 5 is fixed onto the flange 3 via, for example, a support member 25. The sensor 5 uses a magnet to gather the conductive substance contained in the lubricating oil between paired electrodes and uses a change in electrical resistance between the paired electrodes to sense the amount of the conductive substance in the lubricating oil. The sensor 5 may be alternatively positioned, for example, inside the casing 21 but can be at any position within the mechanism 1 as long as the position is within the space containing therein the lubricating oil.

Figure 2:
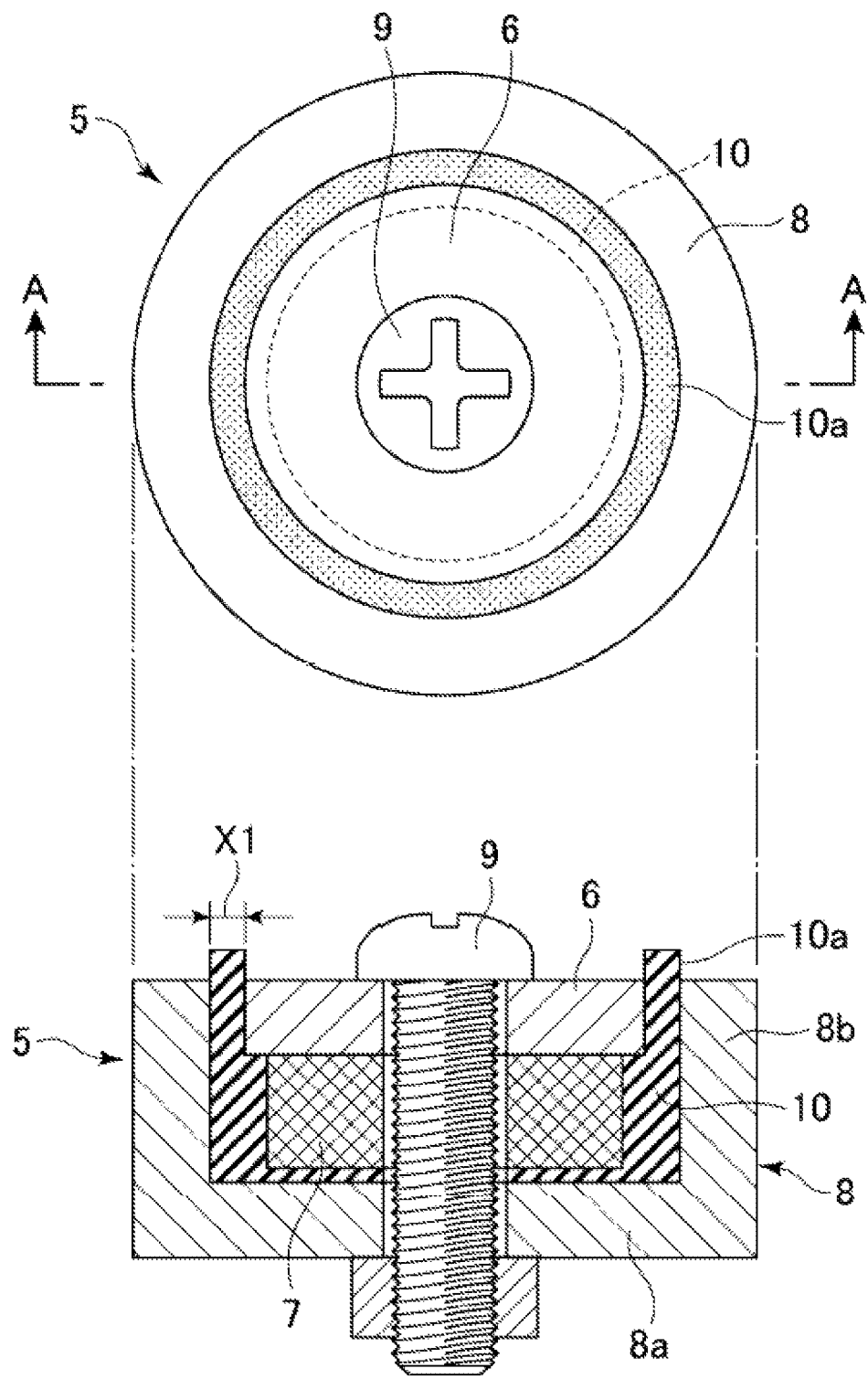
FIG. 2 includes a top view and a sectional view of the sensor relating to the first embodiment of the present invention.

Next, with reference to FIG. 2, a detailed description is given of the structure of the sensor 5. FIG. 2 schematically shows the structure of the sensor relating to the first embodiment of the present invention. FIG. 2 includes a top view of the sensor 5 and a sectional view showing a cross-section along the A-A line in the top view.

As shown in FIG. 2, the sensor 5 has a substantially columnar outer shape and includes a first electrode 6, a magnet 7, a second electrode 8, a fastening member 9, and an attracting portion 10. As shown in FIG. 2, the first electrode 6 has a circular shape when seen from the top surface of the sensor 5 and is positioned at the center of the sensor 5. The second electrode 8 is a bottomed tubular member and includes a bottom portion 8a extending substantially parallel to the first electrode 6 and a wall portion (tubular portion) 8b continuous with the bottom portion 8a and extending substantially perpendicularly to the bottom portion 8a.

The magnet 7 has a substantially columnar shape and is positioned between the first electrode 6 and the bottom portion 8a of the second electrode 8. The first electrode 6, the magnet 7, and the bottom portion 8a of the second electrode 8 each have therein a through hole, through which the fastening member 9 (a bolt in the illustrated embodiment) is inserted. The fastening member 9 is inserted through the through holes, so that the first electrode 6, the magnet 7, and the second electrode 8 are fixed to each other. The first electrode 6 and the second electrode 8 are fixed while being spaced away from each other. The first electrode 6 and the second electrode 8 are made of an electrically conductive magnetic material such as iron, ferrite core and silicon steel. The magnet 7 is, for example, a permanent magnet. Instead of using such a permanent magnet, however, the first electrode 6 may serve both as the magnet and as the electrode.

The attracting portion 10 is provided to fill the space between the first electrode 6 and the second electrode 8 and interposed between the first electrode 6 and the second electrode 8. A distance X1 between the first electrode 6 and the wall portion 8b of the second electrode 8 is larger than the dimension of the conductive substance contained in the lubricating oil. For example, the conductive substance has a dimension of approximately 1.0 µm to 100 µm, and the distance X1 is preferably just large enough to prevent a short circuit from occurring due to iron powder produced by initial wear. In the illustrated embodiment, the magnet 7 is in contact with the first electrode 6 and surrounded by the attracting portion 10. The attracting portion 10 is made of an insulating non-magnetic material, for example, a resin. The magnet 7 forms a magnetic flux line between the first electrode 6 and the second electrode 8. Thus, the conductive substance contained in the lubricating oil is gathered to the vicinity of the attracting portion 10.

The sensor 5 includes a short circuit preventing portion 10a for preventing a short circuit from being caused by a large-diameter conductive piece between the first electrode 6 and the second electrode 8. Here, the large-diameter conductive piece is, for example, foreign matter such as a cutting chip produced by cutting or other methods of processing performed during the manufacturing process of the mechanism 1 (see FIG. 1) and refers to a conductive particle having a dimension larger than the distance X1 between the first electrode 6 and the second electrode 8. By way of an example, the large-diameter conductive piece has a size of approximately 2 mm to 5 mm.

In the embodiment shown in FIG. 2, the short circuit preventing portion 10a is a protrusion on the attracting portion 10 and formed integrally with the attracting portion 10. In other words, the short circuit preventing portion 10a and the attracting portion 10 form a one-piece structure. Therefore, similarly to the attracting portion 10, the short circuit preventing portion 10a is made of an insulating non-magnetic material, for example, a resin. Alternatively, the attracting portion 10 and the short circuit preventing portion 10a may be separate members from each other. In the sectional view of FIG. 2, the short circuit preventing portion 10a has a width substantially equal to the distance X1 between the first electrode 6 and the wall portion 8b of the second electrode 8. When seen from the top surface of the sensor 5, the short circuit preventing portion 10a has an annular shape and entirely surrounds the first electrode 6.

The first electrode 6 and the second electrode 8 are respectively connected to output lines (not shown) and electrically connected to a sensing unit 50 (see FIG. 1) via the output lines.

The sensing unit 50 is configured to sense a change in electrical resistance between the first electrode 6 and the second electrode 8. The sensing unit 50 includes a sensor drive circuit for predicting a failure of the parts constituting the mechanism 1 based on, for example, a change in electrical resistance caused by the gathering of the conductive substance in the vicinity of the attracting portion 10. If the conductive substance contained in the lubricating oil is gathered in the vicinity of the attracting portion 10, this causes a drop in electrical resistance (or a short circuit) between the first electrode 6 and the second electrode 8 to which voltage is being applied, resulting in a change in output level of the output lines. The sensing unit 50 senses such a change in electrical resistance, thereby predicting a failure of the parts constituting the mechanism 1.

The drop in electrical resistance may be indicated by an ON signal and an OFF signal corresponding to electrical disconnection and connection. The sensing unit 50 may sense two states of electrical disconnection and connection (hereinafter, may be referred to as "perform digital sensing"). The sensing unit 50 may be connected to a higher-level control device (not shown) such as a manipulator in a wired or wireless manner. The higher-level control device may be configured to, upon reception of a signal from the sensing unit 50, issue an alert for demanding maintenance of, for example, the speed reducer 2 with a predetermined notifying unit (for example, a display or voice output device).

As described above, the sensor 5 includes the short circuit preventing portion 10a for preventing a short circuit between the first electrode 6 and the second electrode 8 caused by a large-diameter conductive piece having a dimension larger than the distance X1 between the first electrode 6 and the second electrode 8. The short circuit preventing portion 10a is a protrusion on the attracting portion 10. With the protrusion being provided between the first electrode 6 and the second electrode 8 in this manner, even when a large-diameter conductive piece is attracted to the vicinity of the attracting portion 10, the large-diameter conductive piece is prevented from electrically contacting at least one of the first electrode 6 and the second electrode 8. Accordingly, a short circuit can be prevented from being caused by the large-diameter conductive piece between the first electrode 6 and the second electrode 8, resulting in preventing the sensor 5 from operating unexpectedly.

In the sensor 5, the short circuit preventing portion 10a and the attracting portion 10 form a one-piece structure. This reduces the number of parts constituting the sensor 5, so that the sensor 5 can be manufactured easily.

Figure 3:
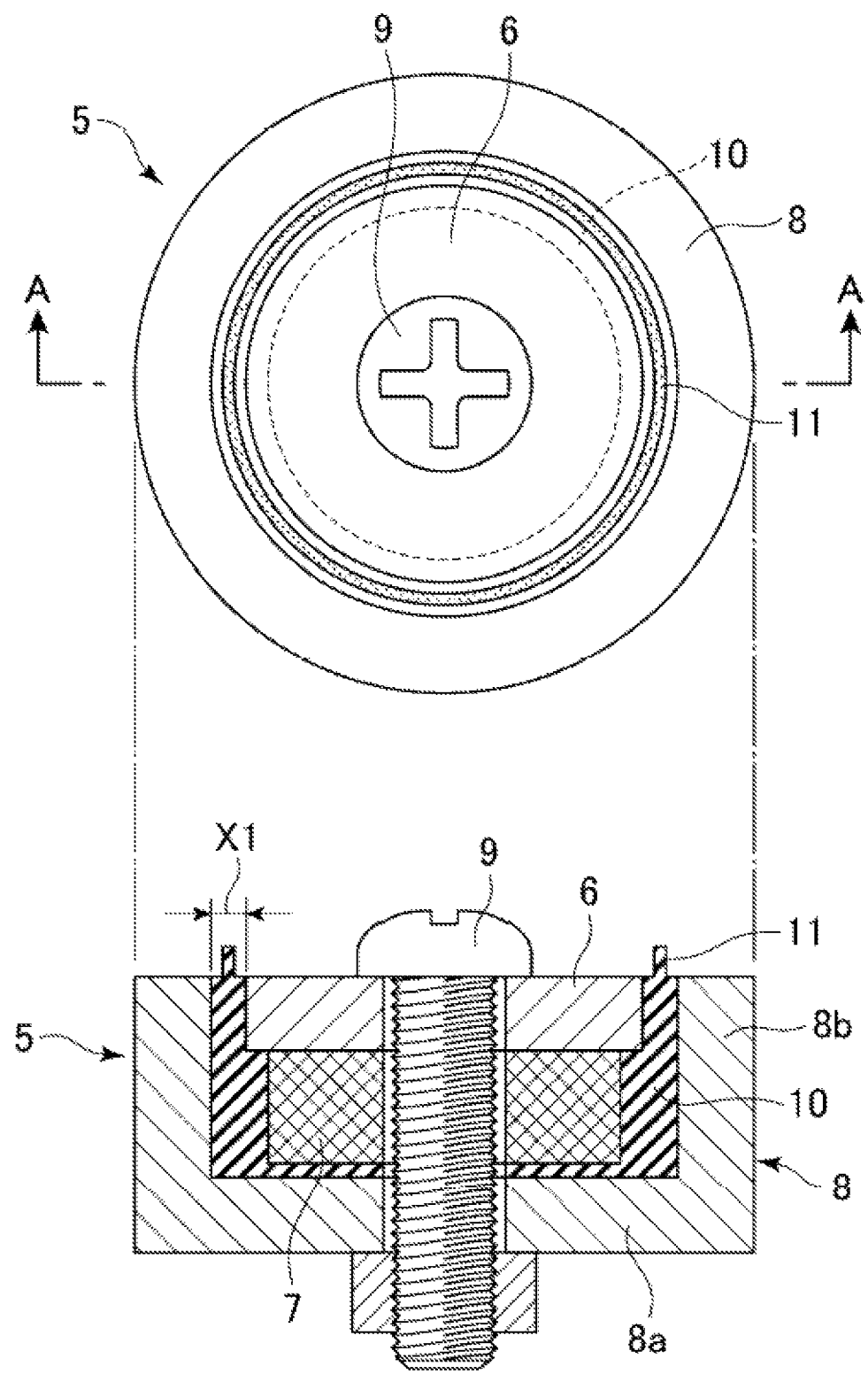
FIG. 3 includes a top view and a sectional view showing a sensor including a short circuit preventing portion relating to a modification example.

Next, with reference to FIG. 3, a description is given of a modification example of the short circuit preventing portion of the sensor 5. As shown in FIG. 3, similarly to the short circuit preventing portion 10a, a short circuit preventing portion 11 relating to a modification example is a protrusion provided on the attracting portion 10 and formed integrally with the attracting portion 10. Similarly to the short circuit preventing portion 10a, the short circuit preventing portion 11 is made of, for example, an insulating non-magnetic material such as a resin. When seen from the top surface of the sensor 5, the short circuit preventing portion 11 has an annular shape and entirely surrounds the first electrode 6. The short circuit preventing portion 11 is different from the short circuit preventing portion 10a in that the short circuit preventing portion 11 has a width smaller than the distance X1 between the first electrode 6 and the wall portion 8b of the second electrode 8.

As described above, in the sensor 5 including the short circuit preventing portion 11 having a width smaller than the distance X1, electrical contact can be also prevented between a large-diameter conductive piece and at least one of the first electrode 6 and the second electrode 8. Accordingly, a short circuit is prevented from being caused by the large-diameter conductive piece between the first electrode 6 and the second electrode 8, resulting in preventing the sensor 5 from operating unexpectedly.

Figure 4:
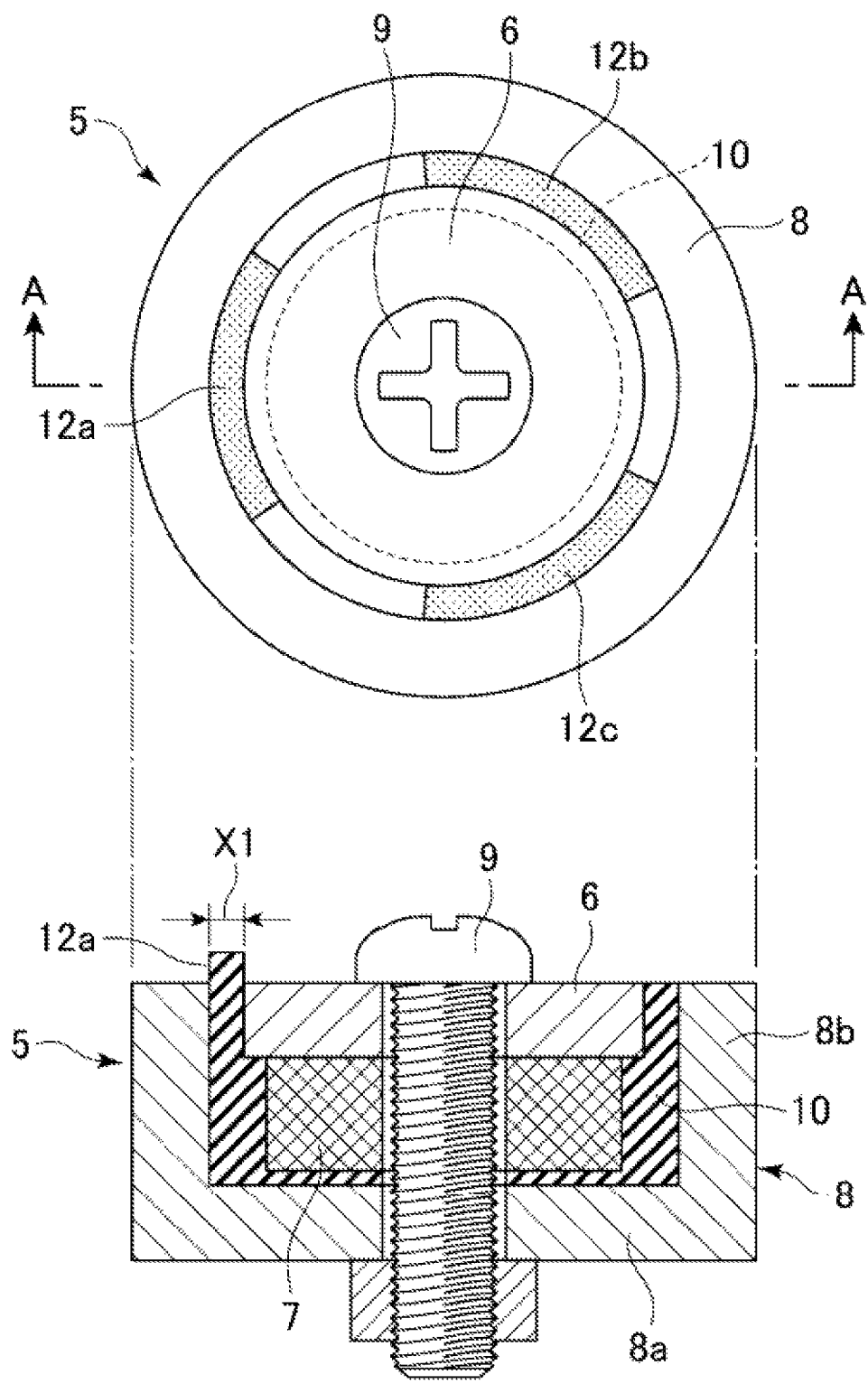
FIG. 4 includes a top view and a sectional view showing a sensor including a short circuit preventing portion relating to another modification example.

Next, with reference to FIG. 4, a description is given of another modification example of a short circuit preventing portion of the sensor 5. As shown in FIG. 4, the short circuit preventing portion of the sensor 5 may be divided into a plurality of portions. In the embodiment shown in FIG. 4, the sensor 5 includes three short circuit preventing portions 12a, 12b and 12c. The short circuit preventing portions 12a, 12b, and 12c are each a protrusion provided on the attracting portion 10 and formed integrally with the attracting portion 10. Similarly to the attracting portion 10, the short circuit preventing portions 12a, 12b and 12c are made of, for example, an insulating non-magnetic material such as a resin. When seen from the top surface of the sensor 5, the short circuit preventing portions 12a, 12b and 12c are spaced at equal intervals from each other around the first electrode 6.

Even if the short circuit preventing portion is divided into a plurality of portions as described above, electrical contact can be prevented between a large-diameter conductive piece and at least one of the first electrode 6 and the second electrode 8 at the positions of the short circuit preventing portions 12a, 12b and 12c. Accordingly, a short circuit can be prevented between the first electrode 6 and the second electrode 8, resulting in preventing the sensor 5 from operating unexpectedly.

Figure 5:
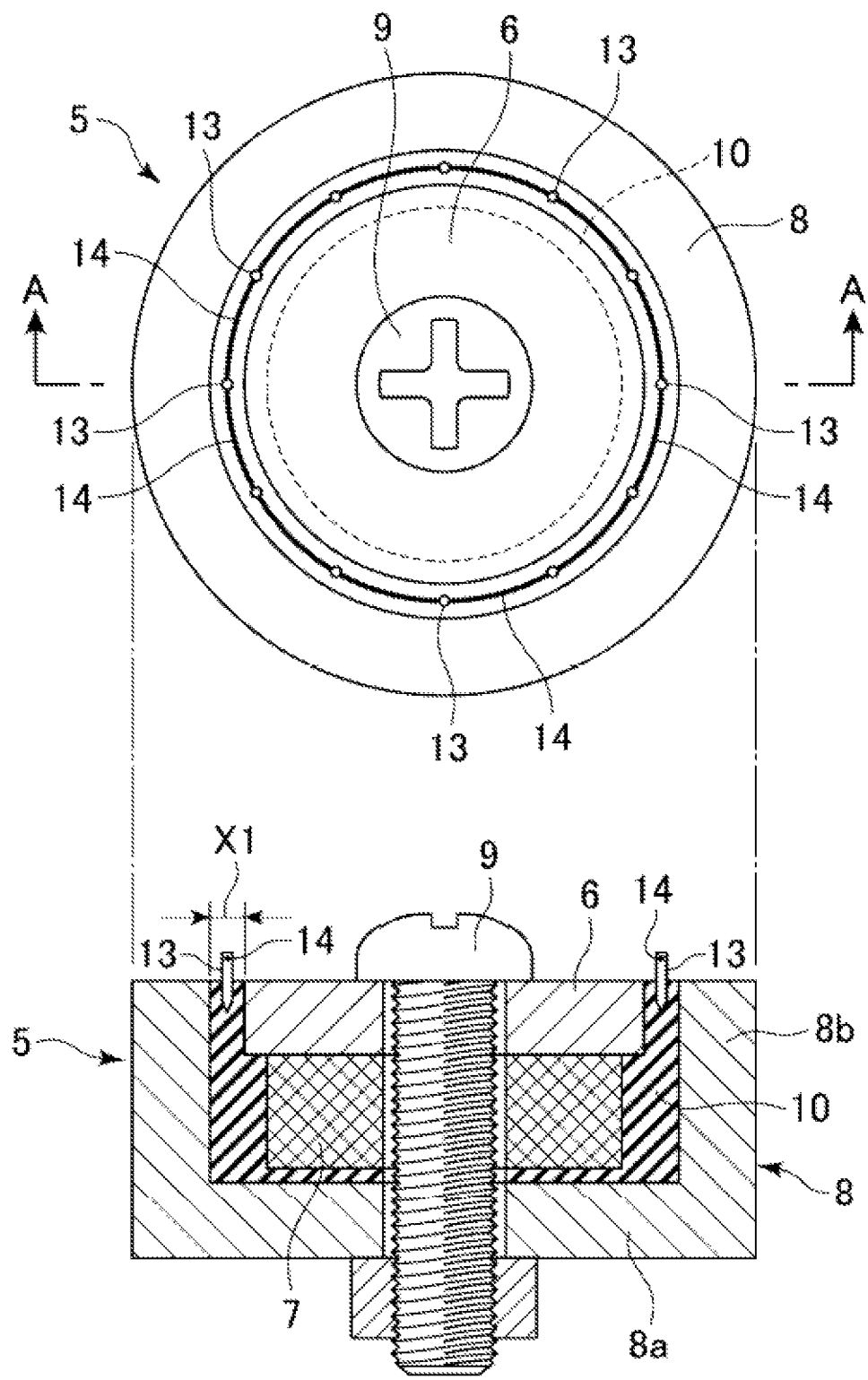
FIG. 5 includes a top view and a sectional view showing a sensor including a short circuit preventing portion relating to still another modification example.

Next, with reference to FIG. 5, a description is given of still another modification example of the short circuit preventing portion of the sensor 5. As shown in FIG. 5, the short circuit preventing portion of the sensor 5 may be a wire 14 extending in the direction intersecting the direction in which the first electrode 6 and the wall portion 8b of the second electrode 8 face each other. The wire 14 is supported by a plurality of support portions 13 and provided on the attracting portion 10 while being spaced away from the attracting portion 10.

In the embodiment shown in FIG. 5, the support portions 13 are each a stake-shaped member. One of the ends of each support portion 13 is fixedly embedded in the attracting portion 10. The other end of each support portion 13 has therein a through hole, through which the wire 14 is inserted. The wire 14 is inserted through the through hole, thus being fixed while being spaced away from the attracting portion 10. When seen from the top surface of the sensor 5, the support portions 13 are spaced at equal intervals from each other in the circumferential direction of the first electrode 6, and the wire 14 entirely surrounds the first electrode 6. There are no particular limitations on the material used to form the wire 14. The wire 14 may be made of a conductive material such as a metal or an insulating material such as a resin.

Even when the short circuit preventing portion is the wire 14 as described above, the wire 14 can also prevent electrical contact between a large diameter conductive piece and at least one of the first electrode 6 and the second electrode 8. Accordingly, a short circuit is prevented from occurring between the first electrode 6 and the second electrode 8, resulting in preventing the sensor 5 from operating unexpectedly.

Figure 6:
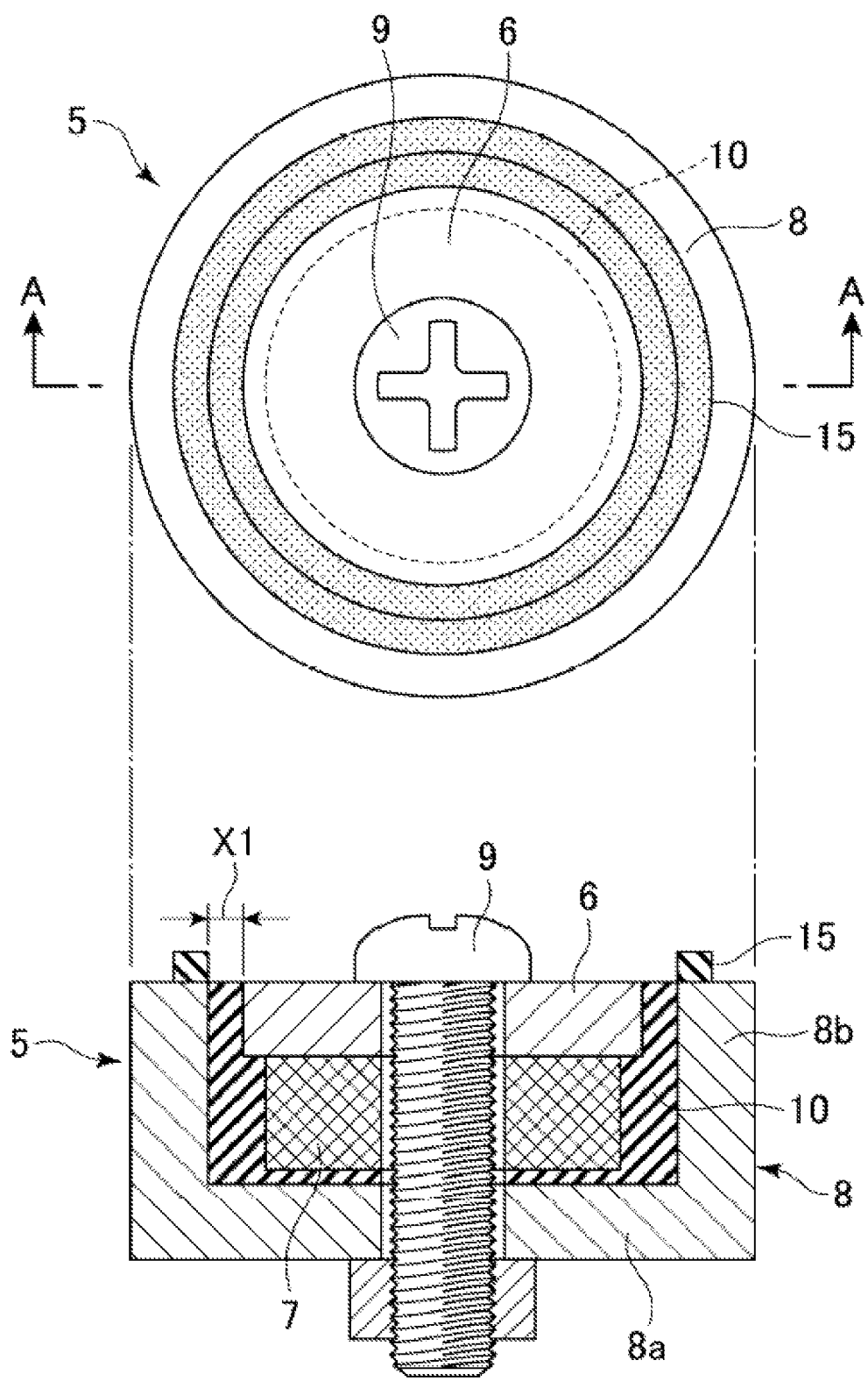
FIG. 6 includes a top view and a sectional view showing a sensor including a short circuit preventing portion relating to a further modification example.

Next, with reference to FIG. 6, a description is given of yet another modification example of the short circuit preventing portion of the sensor 5. As shown in FIG. 6, a short circuit preventing portion 15 relating to the modification example may be an insulating protrusion provided on at least one of the first electrode 6 and the second electrode 8. In the illustrated embodiment, the short circuit preventing portion 15 is provided on the wall portion 8b of the second electrode 8 to extend along the inner edge of the wall portion 8b, where the wall portion 8b is in contact with the attracting portion 10. The short circuit preventing portion 15 may be provided on the first electrode 6 or on both of the first electrode 6 and the second electrode 8.

Even when the short circuit preventing portion 15 is provided on at least one of the first and second electrodes 6 and 8 as described above, the short circuit preventing portion 15 prevents electrical contact between a large diameter conductive piece and at least one of the first electrode 6 and the second electrode 8, similarly to the short circuit preventing portion 10a. Accordingly, a short circuit is prevented from occurring between the first electrode 6 and the second electrode 8, resulting in preventing the sensor 5 from operating unexpectedly.

Figure 7:
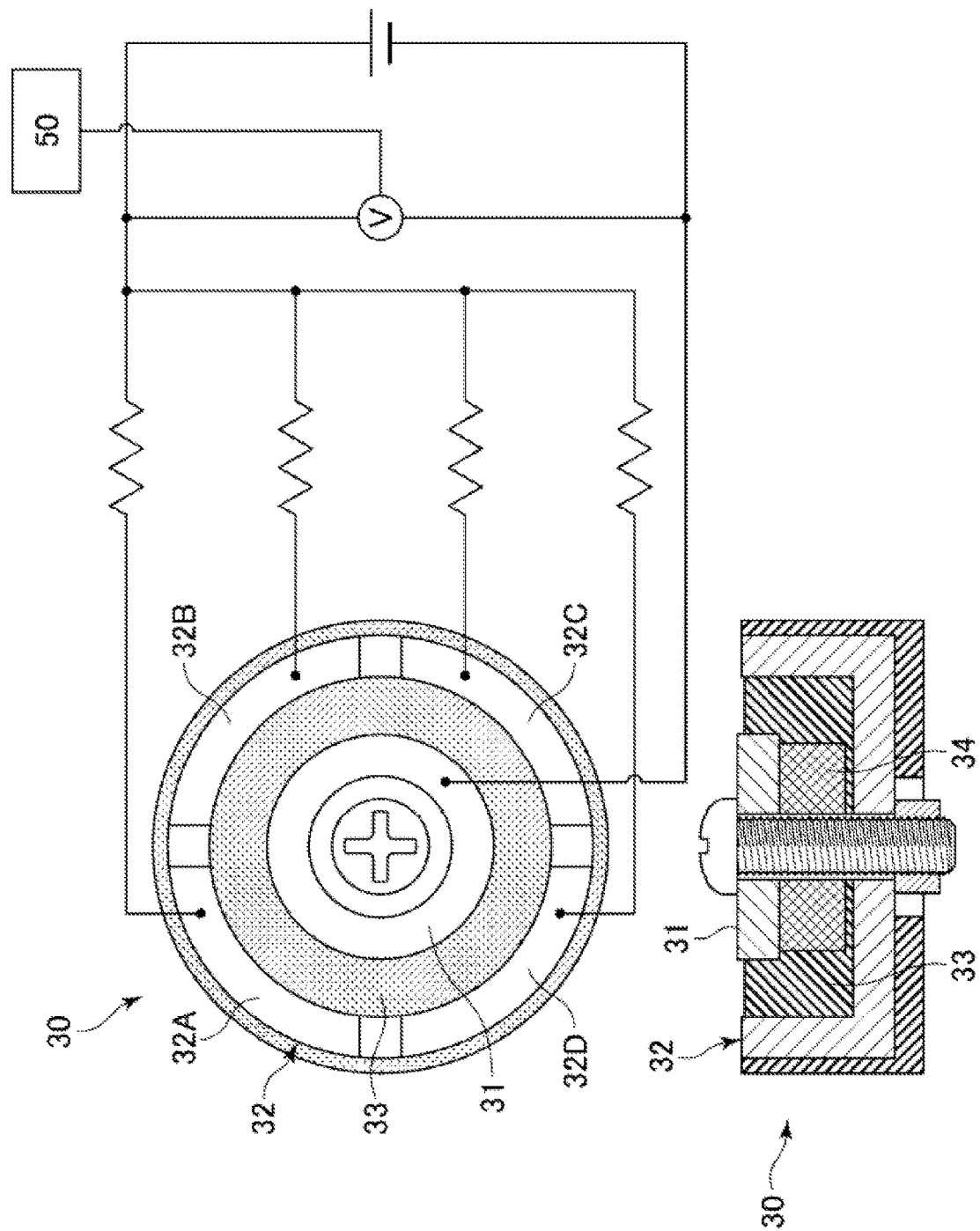
FIG. 7 is used to illustrate a sensor relating to a second embodiment of the present invention.

The following describes a sensor relating to a second embodiment of the present invention with reference to the drawings. FIG. 7 is used to illustrate the sensor relating to the second embodiment. The sensor 30 relating to the second embodiment is configured to sense the amount of a conductive substance contained in a lubricating oil, similarly to the sensor 5 relating to the above-described first embodiment.

The sensor 30 has a substantially columnar outer shape and includes a plurality of detecting units and a sensing unit 50 configured to output a signal when the detecting units experience a change in electrical resistance. More specifically, the sensor 30 includes a center electrode 31, a plurality of outer electrodes 32, an attracting portion 33 disposed between the center electrode 31 and the outer electrodes 32, and a magnet 34. The outer electrodes 32 are insulated from each other. Each of the detecting units is constituted by a pair of electrodes and the attracting portion 33 disposed between the electrodes. The pair of electrodes includes the center electrode 31 and one of the outer electrodes 32.

In the illustrated embodiment, the sensor 30 includes four outer electrodes 32A, 32B, 32C and 32D, and four detecting units are thus formed. There are no particular limitations on the number of the outer electrodes 32 and the number of the detecting units. The magnet 34 of the sensor 30 forms a magnetic flux line between the paired electrodes, so that a conductive substance contained in a lubricating oil is attracted to the attracting portion 33. When the conductive substance is gathered in the vicinity of the attracting portion 33 in this manner, the detecting units experience a change in electrical resistance. While no conductive particles are attracted, the detecting units exhibit the same electrical resistance.

The center electrode 31 and the outer electrodes 32 are respectively connected to output lines, and each detecting unit is electrically connected to the sensing unit 50 via a corresponding one of the output lines. In this embodiment, the detecting units are connected in parallel to each other, and voltage is applied by the same voltage source between the center electrode 31 and each of the outer electrodes 32. The sensing unit 50 outputs a signal if a designated number of detecting units experience a change in electrical resistance. For example, the sensing unit 50 may be configured to output a signal to a higher-level control device such as a manipulator when two or more of the detecting units experience a drop in electrical resistance or when all of the detecting units experience a drop in electrical resistance.

As described above, the sensor 30 includes the plurality of detecting units, and the sensing unit 50 outputs a signal when a designated number of detecting units experience a drop in electrical resistance. In this way, the sensing unit 50 can be configured to output no signal when just one of the detecting units experiences a change in electrical resistance caused by a large-diameter conductive piece. This can prevent the sensor from operating unexpectedly due to a large-diameter conductive piece. Furthermore, in the sensor 30, the sensing unit 50 can be configured to output a signal under a designated condition. Therefore, the single sensor 30 can be configured to output a signal in a timely and optimal manner for individual users, who have different requests for failure prediction timing.

While no conductive particles are attracted, the detecting units are equal in electrical resistance. This can lower the voltage to be applied to the sensor 30.

The detecting units are connected in parallel to each other. This can lower the voltage applied between the paired electrodes in each detecting unit.

Figure 8:
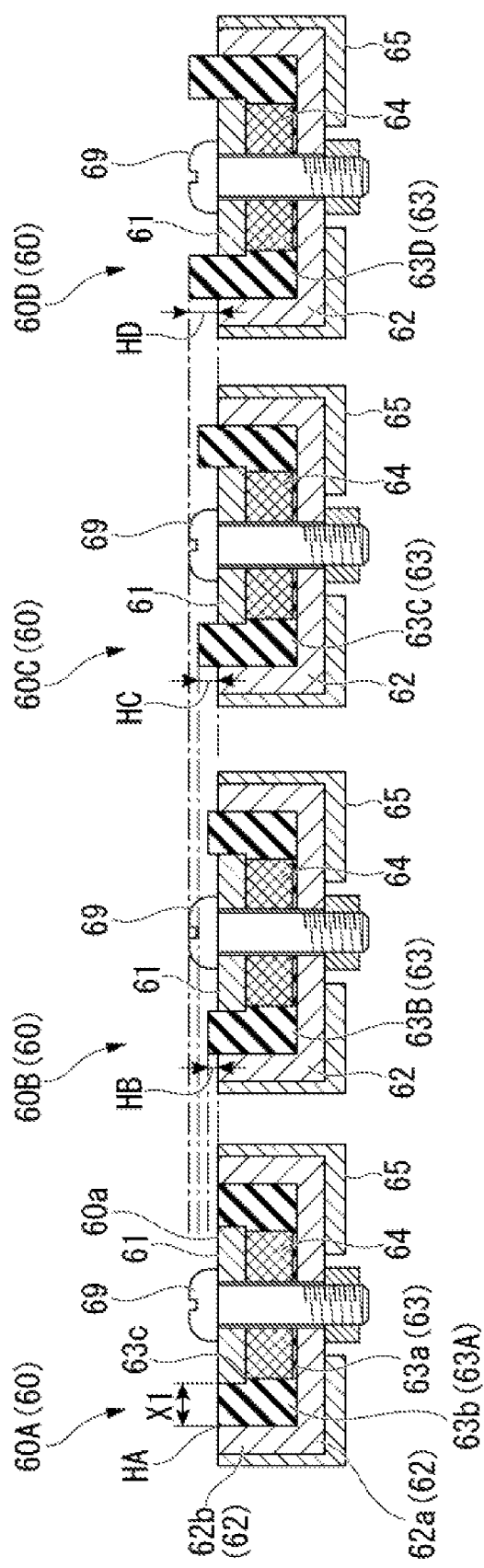
FIG. 8 is a sectional view showing a sensor relating to a third embodiment of the present invention.

The following describes a sensor relating to a third embodiment of the present invention with reference to the drawings. FIG. 8 is a sectional view showing the sensor relating to the present embodiment. The present embodiment is different from the above-described embodiments in terms of the attracting portion. Note that FIG. 8 does not show all of the constituents.

As shown in FIG. 8, a sensor 60 relating to the present embodiment has a substantially columnar outer shape and includes a first electrode (inner electrode) 61, a magnet 64, a second electrode (outer electrode) 62, a fastening member (fastening portion) 69, an attracting portion (insulator) 63 and a casing 65. When seen from the top surface of the sensor 60, the first electrode (inner electrode) 61 has a circular shape and is positioned at the center of the sensor 60. The second electrode (outer electrode) 62 is a bottomed tubular member and has a bottom portion 62*a* extending substantially parallel to the first electrode (inner electrode) 61 and a wall portion (tubular portion) 62*b* continuous with the bottom portion 62*a* and extending substantially perpendicularly to the bottom portion 62*a*. The first electrode (inner electrode) 61 is positioned at the opening of the second electrode (outer electrode) 62.

The magnet 64 has a substantially columnar (substantially disk-shaped) shape and is positioned between the first electrode (inner electrode) 61 and the bottom portion 62*a* of the second electrode (outer electrode) 62. The first electrode (inner electrode) 61, the magnet 64, and the bottom portion 62*a* of the second electrode (outer electrode) 62 each have therein a through hole, through which the fastening member (fastening portion) 69 (a bolt in the illustrated embodiment) is inserted. The fastening member (fastening portion) 69 is inserted through the through hole, so that the first electrode (inner electrode) 61, the magnet 64, and the second electrode (outer electrode) 62 are fixed to each other. The magnet 64 is smaller in outer diameter than the second electrode (outer electrode) 62.

The first electrode (inner electrode) 61 and the second electrode (outer electrode) 62 are fixed while being spaced away from each other. The first electrode (inner electrode) 61 and the second electrode (outer electrode) 62 are, for example, made of an electrically conductive magnetic material such as iron, ferrite core, or silicon steel. The magnet 64 is, for example, a permanent magnet. Instead of using such a permanent magnet, however, the first electrode (inner electrode) 61 may serve both as the magnet and as the electrode.

The attracting portion (insulator) 63 fills the space between the first electrode (inner electrode) 61 and the second electrode (outer electrode) 62 and is interposed between the first electrode (inner electrode) 61 and the second electrode (outer electrode) 62. The attracting portion (insulator) 63 has a bottom portion 63*a* extending along the bottom portion 62*a* of the second electrode (outer electrode) 62 and a tubular portion 63*b* extending along the wall portion (tubular portion) 62*b* of the second electrode (outer electrode) 62. The bottom portion 63*a* and the tubular portion 63*b* are separate members. The bottom portion 63*a* is shaped like a sheet.

The bottom portion 63*a* of the attracting portion (insulator) 63 can be, for example, insulating paper having a thickness of 0.05 to 1 mm. The bottom portion 63*a* of the attracting portion (insulator) 63 can be circular paper having an outer diameter substantially the same as the inner diameter of the tubular portion 63*b*. Alternatively, the bottom portion 63*a* can be circular paper having an outer diameter larger than the inner diameter of the tubular portion 63*b*. In this case, the bottom portion 63*a* can be circular paper having an outer diameter smaller than the outer diameter of the tubular portion 63*b*. Alternatively, the bottom portion 63*a* can be circular paper having an outer diameter same as the outer diameter of the tubular portion 63*b*.

On the inner surface of the tubular portion 63*b* of the attracting portion (insulator) 63, a step 63*c* is formed. In the tubular portion 63*b* of the attracting portion (insulator) 63, the portion on the first electrode (inner electrode) 61 side with respect to the step 63*c* has an inner diameter equal to the outer diameter of the first electrode (inner electrode) 61. In the tubular portion 63*b* of the attracting portion (insulator) 63, the portion on the magnet 64 side with respect to the step 63*c* has an inner diameter equal to the outer diameter of the magnet 64.

The thickness of the end of the tubular portion 63*b* of the attracting portion (insulator) 63, in other words, the distance X1 between the first electrode (inner electrode) 61 and the wall portion 62*b* of the second electrode (outer electrode) 62 is larger than the dimension of the conductive substance contained in the lubricating oil. For example, the conductive substance has a dimension of approximately 1.0 μm to 100 μm, and the distance X1 is preferably just large enough to prevent a short circuit from occurring due to iron powder produced by initial wear. In the illustrated embodiment, the magnet 64 is in contact with the first electrode (inner electrode) 61 and surrounded by the attracting portion (insulator) 63.

The attracting portion (insulator) 63 is made of, for example, an insulating non-magnetic material such as a resin. The magnet 64 forms a magnetic flux line between the first electrode (inner electrode) 61 and the second electrode (outer electrode) 62. Thus, the conductive substance contained in the lubricating oil is gathered to the vicinity of the attracting portion (insulator) 63. Note that the term "detection region" denotes the region within which the lubricating oil circulates.

In the sensor 60 relating to the present embodiment, a sensing plane 60*a* denotes the plane connecting the end of the second electrode (outer electrode) 62 and the surface of the first electrode (inner electrode) 61, which are substantially flush with each other. In other words, on the sensing plane 60*a*, conductive abrasion powder is attracted between the first electrode (inner electrode) 61 and the second electrode (outer electrode) 62 by the magnetic flux line, so that the first electrode (inner electrode) 61 and the second electrode (outer electrode) 62 are electrically connected. This causes a change in resistance between the first electrode (inner electrode) 61 and the second electrode (outer electrode) 62, which is to be detected. Note that the first electrode (inner electrode) 61 may not need to be flush with the opening of the second electrode (outer electrode) 62.

As the creepage distance between the first electrode (inner electrode) 61 and the second electrode (outer electrode) 62 increases, the amount of conductive abrasion powder required to be attracted to lower the resistance to a threshold value or to cause a short circuit between the first electrode (inner electrode) 61 and the second electrode (outer electrode) 62 increases. As the creepage distance between the first electrode (inner electrode) 61 and the second electrode (outer electrode) 62 decreases, the amount of conductive abrasion powder required to be attracted to lower the resistance to a threshold value or to cause a short circuit between the first electrode (inner electrode) 61 and the second electrode (outer electrode) 62 decreases.

The sensor 60 relating to the present embodiment has a sensitivity adjusting unit for adjusting the attraction of the conductive abrasion powder to change the sensitivity. In the present embodiment, the sensitivity adjusting unit is the attracting portion (insulator) 63. More specifically, in the present embodiment, the sensitivity adjusting unit is the tubular portion 63b of the attracting portion (insulator) 63.

The attracting portion (insulator) 63 of the present embodiment is capable of adjusting the creepage distance between the first electrode (inner electrode) 61 and the second electrode (outer electrode) 62 to adjust the amount of conductive abrasion powder to be attracted by the attracting portion (insulator) 63. Specifically, a group of attracting portions (insulators) 63 are provided that have tubular portions 63b with different protruding heights with respect to the sensing plane 60a, as shown in FIG. 8. In the sensor 60A shown in FIG. 8, the sensing plane 60a is at the same level as the end of the tubular portion 63b of an attracting portion (insulator) 63A or at a height HA. In other words, the sensing plane 60a is flush with the tubular portion 63b of the attracting portion (insulator) 63A.

In the sensor 60B shown in FIG. 8, the end of the tubular portion 63b of an attracting portion (insulator) 63B is higher than the sensing plane 60a by a height HB, in other words, the tubular portion 63b of the attracting portion (insulator) 63B protrudes with respect to the sensing plane 60a by the height HB. In the sensor 60C shown in FIG. 8, the end of the tubular portion 63b of an attracting portion (insulator) 63C is higher than the sensing plane 60a by a height HC, in other words, the tubular portion 63b of the attracting portion (insulator) 63C protrudes with respect to the sensing plane 60a by the height HC. In the sensor 60D shown in FIG. 8, the end of the tubular portion 63b of an attracting portion (insulator) 63D is higher than the sensing plane 60a by a height HD, in other words, the tubular portion 63b of the attracting portion (insulator) 63D protrudes with respect to the sensing plane 60a by the height HD.

Here, the heights HA, HB, HC and HD are related to each other as follows:

$$HA(=0) < HB < HC < HD.$$

The sensor 60 relating to the present embodiment has a group of attracting portions (insulators) 63 that are different in the value of the tubular portion 63b as described above. The sensor 60 relating to the present embodiment can be assembled with a selected one of the attracting portions. This means that the group of attracting portions (insulators) 63 that are different in the height (axial dimension) of the tubular portion 63b serves as the sensitivity adjusting unit. In this way, the creepage distance between the first electrode (inner electrode) 61 and the second electrode (outer electrode) 62 can be selected from among a plurality of values by making a selection in the sensitivity adjusting unit.

A reference creepage distance denotes the creepage distance in the sensor 60A shown in FIG. 8 between the first electrode (inner electrode) 61 and the second electrode (outer electrode) 62, which is defined by the end of the tubular portion 63b of the attracting portion (insulator) 63A.

In the sensor 60B shown in FIG. 8, the creepage distance between the first electrode (inner electrode) 61 and the second electrode (outer electrode) 62, which is defined by the end of the tubular portion 63b of the attracting portion (insulator) 63B, is longer than the reference creepage distance. Accordingly, a larger amount of conductive abrasion powder can be attracted before the resistance between the first electrode (inner electrode) 61 and the second electrode (outer electrode) 62 drops to a threshold value or before a short circuit occurs. In this way, for example, even when the speed reducer 2 has a large size and thus produces an increased amount of initial abrasion powder, the sensor 60B can reliably sense the failure of the speed reducer 2 without being affected by the increased amount of initial abrasion powder.

In the sensor 60C shown in FIG. 8, the creepage distance between the first electrode (inner electrode) 61 and the second electrode (outer electrode) 62, which is defined by the end of the tubular portion 63b of the attracting portion (insulator) 63C, is longer than in the sensor 60B. Accordingly, a further larger amount of conductive abrasion powder can be attracted before the resistance between the first electrode (inner electrode) 61 and the second electrode (outer electrode) 62 drops to a threshold value or before a short circuit occurs. In this way, even when the speed reducer 2 has a further larger size and thus produces an increased amount of initial abrasion powder, the sensor 60C can reliably sense the failure of the speed reducer 2 without being affected by the increased amount of initial abrasion powder.

In the sensor 60D shown in FIG. 8, the creepage distance between the first electrode (inner electrode) 61 and the second electrode (outer electrode) 62, which is defined by the end of the tubular portion 63b of the attracting portion (insulator) 63D, is longer than in the sensor 60C. Accordingly, a further larger amount of conductive abrasion powder can be attracted before the resistance between the first electrode (inner electrode) 61 and the second electrode (outer electrode) 62 drops to a threshold value or before a short circuit occurs. In this way, even when the speed reducer 2 has a further larger size and thus produces an increased amount of initial abrasion powder, the sensor 60D can reliably sense the failure of the speed reducer 2 without being affected by the increased amount of initial abrasion powder.

As described above, the sensor 60 can reliably sense the failure of the speed reducer 2 by selecting an appropriate one of the attracting portions (insulators) 63 without the need of increasing the size of the sensor 60 and also without affecting the other constituents. In other words, the sensor 60 can achieve different levels of sensitivity by replacing only the attracting portion (insulator) 63 while using the center electrode (inner electrode) 61, the external electrode (outer electrode) 62, the magnet 64, the casing 65 and the fastening member (fastening portion) 69 in common.

In the present embodiment described above, four different attracting portions (insulators) 63 are employed as the sensitivity adjusting unit, but the present invention is not limited to such and the number can be determined appropriately.

The sensor 60 relating to the present embodiment can be assembled in the following manner.

To start with, the external electrode (outer electrode) 62 is placed within the casing 65. Subsequently, the bottom portion 63a of the attracting portion (insulator) 63 is positioned on the bottom portion 62a of the external electrode (outer electrode) 62. Following this, the tubular portion 63b of the attracting portion (insulator) 63 having a selected height is inserted into the external electrode (outer electrode) 62. Subsequently, the magnet 64 is inserted into the tubular portion 63b, and the center electrode (inner electrode) 61 is further inserted. At this stage, the fastening member (fastening portion) 69 is inserted and fixedly fastened. In this way, the sensor 60 is assembled.

Having the sensitivity adjusting unit, the sensor 60 relating to the present embodiment is capable of setting the sensitivity at a predetermined level. Specifically, when a large amount of conductive abrasion powder is expected to be produced, the sensitivity adjusting unit can be selected such that a larger creepage distance to attract the abrasion powder can be obtained between the electrode 61 and the electrode 62 to set the sensitivity of the sensor 60 at a predetermined level. In addition, when a small amount of conductive abrasion powder is expected to be produced, the sensitivity adjusting unit can be selected such that a smaller creepage distance to attract the abrasion powder can be obtained between the electrode 61 and the electrode 62 to set the sensitivity of the sensor 60 at a predetermined level. In this way, the sensor 60 can reliably sense a failure of the speed reducer 2 without being affected by the increased amount of initial abrasion powder produced by the speed reducer 2.

Speed reducers of different models (sizes) may produce different amounts of iron powder (abrasion powder) during the initial wear period. In the case of large speed reducers, a large amount of initial abrasion iron powder is produced, and the initial abrasion iron powder may fill the electrical gap in the sensor between the electrodes 61 and 62. If such is the case, the sensor may react and erroneously operate. Therefore, the electrical gap in the sensor needs to be determined considering the model of the speed reducer, but this requirement may disadvantageously result in a larger sensor size in the diameter direction. To address this issue, the sensor 60 relating to the present embodiment has a sensitivity adjusting unit, which includes attracting portions (insulators) 63 with different heights. This configuration produces the same effects as the enlargement of the sensor in the diameter direction and thus allows the sensor 60 to maintain the size.

Figure 9:
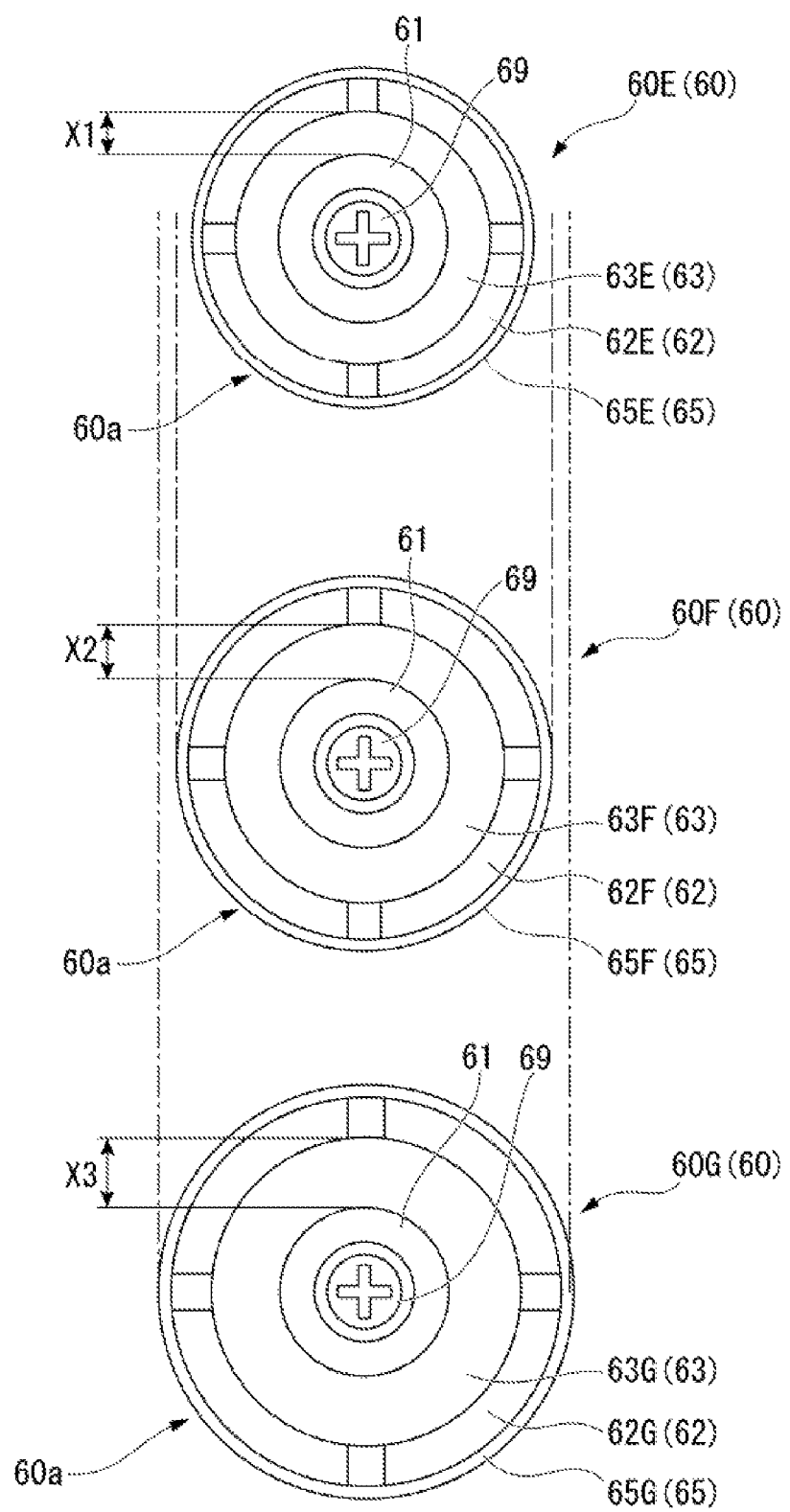
FIG. 9 is a top view showing a sensor relating to a fourth embodiment of the present invention.

The following describes a sensor relating to a fourth embodiment of the present invention with reference to the drawings. FIG. 9 is a top view showing the sensor relating to the present embodiment. The present embodiment is different from the above-described third embodiment in terms of the attracting portion and outer electrode. FIG. 9 does not show all of the constituents.

As shown in FIG. 9, the sensor 60 relating to the present embodiment has a substantially columnar outer shape and includes a first electrode (inner electrode) 61, a magnet 64, a second electrode (outer electrode) 62, a fastening member (fastening portion) 69, an attracting portion (insulator) 63 and a casing 65. When seen from the top surface of the sensor 60, the first electrode (inner electrode) 61 has a circular shape and is positioned at the center of the sensor 60. The second electrode (outer electrode) 62 is a bottomed tubular member and has a bottom portion 62*a* extending substantially parallel to the first electrode (inner electrode) 61 and a wall portion (tubular portion) 62*b* continuous with the bottom portion 62*a* and extending substantially perpendicularly to the bottom portion 62*a*.

The magnet 64 has a substantially columnar (substantially disk-shaped) shape and is positioned between the first electrode (inner electrode) 61 and the bottom portion 62*a* of the second electrode (outer electrode) 62. The first electrode (inner electrode) 61, the magnet 64, and the bottom portion 62*a* of the second electrode (outer electrode) 62 each have therein a through hole, through which the fastening member (fastening portion) 69 (a bolt in the illustrated embodiment) is inserted. The fastening member (fastening portion) 69 is inserted through the through hole, so that the first electrode (inner electrode) 61, the magnet 64, and the second electrode (outer electrode) 62 are fixed to each other. The magnet 64 is smaller in outer diameter than the second electrode (outer electrode) 62.

The first electrode (inner electrode) 61 and the second electrode (outer electrode) 62 are fixed while being spaced away from each other. The first electrode (inner electrode) 61 and the second electrode (outer electrode) 62 are, for example, made of an electrically conductive magnetic material such as iron, ferrite core, or silicon steel. The magnet 64 is, for example, a permanent magnet. Instead of using such a permanent magnet, however, the first electrode (inner electrode) 61 may serve both as the magnet and as the electrode.

The attracting portion (insulator) 63 fills the space between the first electrode (inner electrode) 61 and the second electrode (outer electrode) 62 and is interposed between the first electrode (inner electrode) 61 and the second electrode (outer electrode) 62. The attracting portion (insulator) 63 has a bottom portion 63*a* extending along the bottom portion 62*a* of the second electrode (outer electrode) 62 and a tubular portion 63*b* extending along the wall portion (tubular portion) 62*b* of the second electrode (outer electrode) 62. The bottom portion 63*a* and the tubular portion 63*b* are separate members. The bottom portion 63*a* is shaped like a sheet.

The bottom portion 63*a* of the attracting portion (insulator) 63 can be, for example, insulating paper having a thickness of 0.05 to 1 mm. The bottom portion 63*a* of the attracting portion (insulator) 63 can be circular paper having an outer diameter substantially the same as the inner diameter of the tubular portion 63*b*. Alternatively, the bottom portion 63*a* can be circular paper having an outer diameter larger than the inner diameter of the tubular portion 63*b*. In this case, the bottom portion 63*a* can be circular paper having an outer diameter smaller than the outer diameter of the tubular portion 63*b*. Alternatively, the bottom portion 63*a* can be circular paper having an outer diameter same as the outer diameter of the tubular portion 63*b*.

On the inner surface of the tubular portion 63*b* of the attracting portion (insulator) 63, a step 63*c* is formed. In the tubular portion 63*b* of the attracting portion (insulator) 63, the portion on the first electrode (inner electrode) 61 side with respect to the step 63*c* has an inner diameter equal to the outer diameter of the first electrode (inner electrode) 61. In the tubular portion 63*b* of the attracting portion (insulator) 63, the portion on the magnet 64 side with respect to the step 63*c* has an inner diameter equal to the outer diameter of the magnet 64.

The thickness of the end of the tubular portion 63*b* of the attracting portion (insulator) 63, in other words, the distance X1 between the first electrode (inner electrode) 61 and the wall portion 62*b* of the second electrode (outer electrode) 62 is larger than the dimension of the conductive substance contained in the lubricating oil. For example, the conductive substance has a dimension of approximately 1.0 μm to 100 μm, and the distance X1 is preferably just large enough to prevent a short circuit from occurring due to iron powder produced by initial wear. In the illustrated embodiment, the magnet 64 is in contact with the first electrode (inner electrode) 61 and surrounded by the attracting portion (insulator) 63.

The attracting portion (insulator) 63 is, for example, made of an insulating non-magnetic material such as a resin. The magnet 64 forms a magnetic flux line between the first electrode (inner electrode) 61 and the second electrode (outer electrode) 62. In this way, the conductive substance contained in the lubricating oil is gathered to the vicinity of the attracting portion (insulator) 63.

In the sensor 60 relating to the present embodiment, a sensing plane 60a denotes the plane connecting the end of the second electrode (outer electrode) 62 and the surface of the first electrode (inner electrode) 61, which are substantially flush with each other. In other words, on the sensing plane 60a, conductive abrasion powder is attracted between the first electrode (inner electrode) 61 and the second electrode (outer electrode) 62 by the magnetic flux line, so that the first electrode (inner electrode) 61 and the second electrode (outer electrode) 62 are electrically connected. This causes a change in resistance between the first electrode (inner electrode) 61 and the second electrode (outer electrode) 62, which is to be detected.

As the creepage distance between the first electrode (inner electrode) 61 and the second electrode (outer electrode) 62 increases, the amount of conductive abrasion powder required to be attracted to lower the resistance to a threshold value or to cause a short circuit between the first electrode (inner electrode) 61 and the second electrode (outer electrode) 62 increases. As the creepage distance between the first electrode (inner electrode) 61 and the second electrode (outer electrode) 62 decreases, the amount of conductive abrasion powder required to be attracted to lower the resistance to a threshold value or to cause a short circuit between the first electrode (inner electrode) 61 and the second electrode (outer electrode) 62 decreases.

The sensor 60 relating to the present embodiment has a sensitivity adjusting unit for adjusting the attraction of the conductive abrasion powder to change the sensitivity. In the present embodiment, the sensitivity adjusting unit is the attracting portion (insulator) 63. More specifically, in the present embodiment, the sensitivity adjusting unit is the tubular portion 63b of the attracting portion (insulator) 63, the external electrode (outer electrode) 62 and the casing 65.

The attracting portion (insulator) 63 of the present embodiment is capable of adjusting the creepage distance between the first electrode (inner electrode) 61 and the second electrode (outer electrode) 62 considering the large-diameter conductive chip to adjust the amount of the conductive abrasion powder to be attracted by the attracting portion (insulator) 63. Specifically, as shown in FIG. 9, a group of attracting portions (insulators) 63 are provided that are different in the radial thickness of the tubular portion 63b. A sensor 60E shown in FIG. 9 has an attracting portion (insulator) 63E, whose tubular portion 63b has an end with a thickness X1 on the sensing plane 60a, in other words, which provides a distance X1 on the sensing plane 60a between the first electrode (inner electrode) 61 and the wall portion 62b of the second electrode (outer electrode) 62. The sensor 60E includes an external electrode (outer electrode) 62E and a casing 65E having a radial dimension corresponding to the attracting portion (insulator) 63E.

A sensor 60F shown in FIG. 9 has an attracting portion (insulator) 63F, whose tubular portion 63b has an end with a thickness X2 on the sensing plane 60a, in other words, which provides a distance X2 on the sensing plane 60a between the first electrode (inner electrode) 61 and the wall portion 62b of the second electrode (outer electrode) 62. The sensor 60F includes an external electrode (outer electrode) 62F and a casing 65F having a radial dimension corresponding to the attracting portion (insulator) 63F. A sensor 60G shown in FIG. 9 has an attracting portion (insulator) 63G, whose tubular portion 63b has an end with a thickness X3 on the sensing plane 60a, in other words, which provides a distance X3 on the sensing plane 60a between the first electrode (inner electrode) 61 and the wall portion 62b of the second electrode (outer electrode) 62. The sensor 60G includes an external electrode (outer electrode) 62G and a casing 65G having a radial dimension corresponding to the attracting portion (insulator) 63G.

Here, the thicknesses X1, X2 and X3 are related to each other as follows:

$$X1 < X2 < X3.$$

The sensor 60 relating to the present embodiment has a group of attracting portions (insulators) 63 that are different in the value of the tubular portion 63b as described above. The sensor 60 relating to the present embodiment can be assembled with a selected one of the attracting portions. This means that the group of attracting portions (insulators) 63 that are different in the thickness (radial dimension) of the tubular portion 63b serves as the sensitivity adjusting unit. In this way, the creepage distance between the first electrode (inner electrode) 61 and the second electrode (outer electrode) 62 can be selected from among a plurality of values by making a selection in the sensitivity adjusting unit.

A reference creepage distance denotes the creepage distance in the sensor 60E shown in FIG. 9 between the first electrode (inner electrode) 61 and the second electrode (outer electrode) 62E, which is defined by the end of the tubular portion 63b of the attracting portion (insulator) 63E.

In the sensor 60F shown in FIG. 9, the creepage distance between the first electrode (inner electrode) 61 and the second electrode (outer electrode) 62F, which is defined by the end of the tubular portion 63b of the attracting portion (insulator) 63F, is longer than the reference creepage distance. Accordingly, a larger amount of conductive abrasion powder can be attracted before the resistance between the first electrode (inner electrode) 61 and the second electrode (outer electrode) 62F drops to a threshold value or to cause a short circuit. In this way, for example, even when the speed reducer 2 has a large size and thus produces an increased amount of initial abrasion powder, the sensor 60F can reliably sense the failure of the speed reducer 2 without being affected by the increased amount of initial abrasion powder.

In the sensor 60G shown in FIG. 9, the creepage distance between the first electrode (inner electrode) 61 and the second electrode (outer electrode) 62G, which is defined by the end of the tubular portion 63b of the attracting portion (insulator) 63G, is longer than in the sensor 60F. Accordingly, a further larger amount of conductive abrasion powder can be attracted before the resistance between the first electrode (inner electrode) 61 and the second electrode (outer electrode) 62G drops to a threshold value or to cause a short circuit. In this way, even when the speed reducer 2 has a further larger size and thus produces an increased amount of initial abrasion powder, the sensor 60G can reliably sense the failure of the speed reducer 2 without being affected by the increased amount of initial abrasion powder.

As described above, the sensor 60 can reliably sense the failure of the speed reducer 2 by selecting an appropriate one of the attracting portions (insulators) 63 without the need of increasing the axial size of the sensor 60 and also without affecting the center electrode (inner electrode) 61, the magnet 64 and the fastening member (fastening portion) 69. In other words, the sensor 60 can achieve different levels of sensitivity by replacing the attracting portion (insulator) 63, the external electrode (outer electrode) 62 and the casing 65 while using the center electrode (inner electrode) 61, the magnet 64 and the fastening member (fastening portion) 69 in common.

In the present embodiment described above, three different attracting portions (insulators) 63 are employed as the sensitivity adjusting unit, but the present invention is not limited to such and the number can be determined appropriately.

The sensor 60 relating to the present embodiment can be assembled in the following manner.

To start with, the external electrode (outer electrode) 62 is placed within the casing 65 having a selected radial dimension. Subsequently, the bottom portion 63a of the attracting portion (insulator) 63 having a corresponding radial dimension is placed on the bottom portion 62a of the external electrode (outer electrode) 62. Following this, the tubular portion 63b of the attracting portion (insulator) 63 having a selected radial dimension is inserted into the external electrode (outer electrode) 62. Subsequently, the magnet 64 is inserted into the tubular portion 63b, and the center electrode (inner electrode) 61 is further inserted. At this stage, the fastening member (fastening portion) 69 is inserted and fixedly fastened, so that the sensor 60 is assembled. Here, the set of the casing 65, external electrode (outer electrode) 62, attracting portion (insulator) 63 having the selected radial dimension can be alternatively assembled together in advance.

Having the sensitivity adjusting unit, the sensor 60 relating to the present embodiment is capable of setting the sensitivity at a predetermined level. Specifically, when a large amount of conductive abrasion powder is expected to be produced, the sensitivity adjusting unit can be selected such that a larger creepage distance to attract the abrasion powder can be obtained between the electrode 61 and the electrode 62 to set the sensitivity of the sensor 60 at a predetermined level. In addition, when a small amount of conductive abrasion powder is expected to be produced, the sensitivity adjusting unit can be selected such that a smaller creepage distance to attract the abrasion powder can be obtained between the electrode 61 and the electrode 62 to set the sensitivity of the sensor 60 at a predetermined level. In this way, the sensor 60 can reliably sense the failure of the speed reducer 2 without being affected by the increased amount of initial abrasion powder produced by the speed reducer 2.

Figure 10:
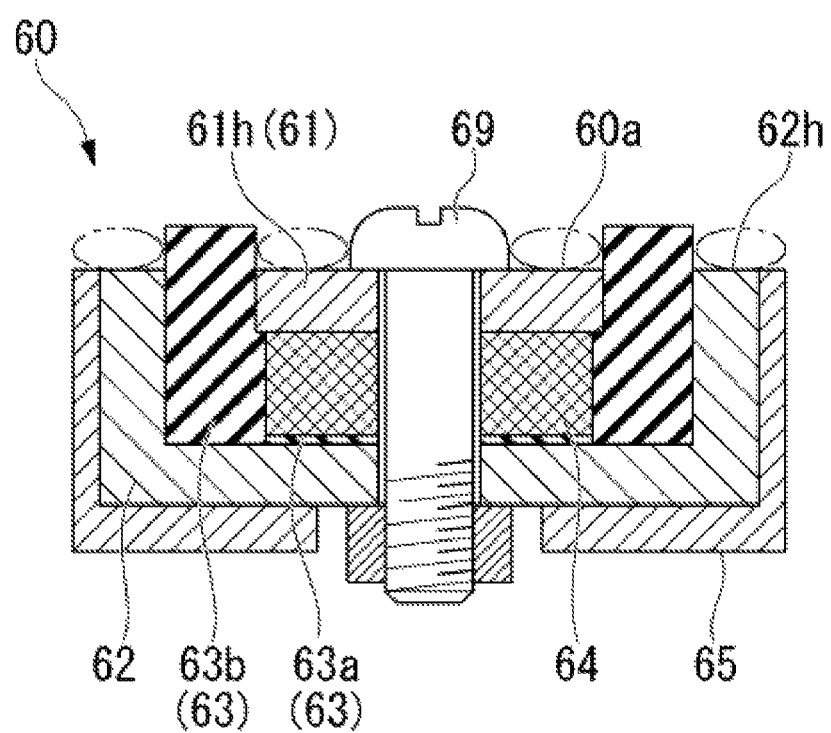
FIG. 10 is a sectional view showing a sensor relating to a fifth embodiment of the present invention.

The following describes a sensor relating to a fifth embodiment of the present invention with reference to the drawings. FIG. 10 is a sectional view showing the sensor relating to the present embodiment. The present embodiment is different from the above-described third and fourth embodiments in terms of the electrodes. FIG. 10 does not show all of the constituents.

The sensor 60 relating to the present embodiment is configured in substantially the same manner as the sensors 60 relating to the third and fourth embodiments, as shown in FIG. 10. The sensor 60 relating to the present embodiment has a sensitivity adjusting unit for adjusting attraction of conductive abrasion powder to change the sensitivity.

In the present embodiment, the sensitivity adjusting unit is the first electrode (inner electrode) 61 and the second electrode (outer electrode) 62. The first electrode (inner electrode) 61 of the present embodiment has a surface treatment layer 61h formed thereon. The second electrode (outer electrode) 62 of the present embodiment has a surface treatment layer 62h formed thereon.

The surface treatment layers 61h and 62h both exhibit excellent slippery and non-adhesive properties and additionally have electrical conductivity, smoothness, lubricity and low adhesiveness. The surface treatment layers 61h and 62h can be formed of, for example, fluororesin electroless nickel composite plating or the like. Here, the fluororesin can be polytetrafluoroethylene particles or the like.

Here, sludge may possibly reduce the amount of abrasion powder to be attracted by the first electrode (inner electrode) 61 and the second electrode (outer electrode) 62. The surface treatment layers 61h and 62h can prevent the sludge from adhering to the first electrode (inner electrode) 61, the second electrode (outer electrode) 62, and the sensing plane 60a and resultantly from reducing the amount of abrasion powder to be attracted between the first electrode (inner electrode) 61 and the second electrode (outer electrode) 62. In this way, the sensitivity of the sensor 60 can be set at a predetermined level. In FIG. 10, the dotted lines indicate the adhering sludge.

Without the surface treatment layers 61h and 62h, the sludge produced by the lubricant accumulates on the electrodes of the sensor to form an insulating coating, which may possibly cause the sensor 60 to malfunction. To address this issue, the present embodiment includes the surface treatment layers 61h and 62h. The surface treatment layers 61h and 62h can improve the slipperiness, thereby achieving excellent flow of the lubricant. As a result, the sludge can be prevented from accumulating and the sensor 60 can be thus expected to predict a failure in a stable manner.

Figure 11:
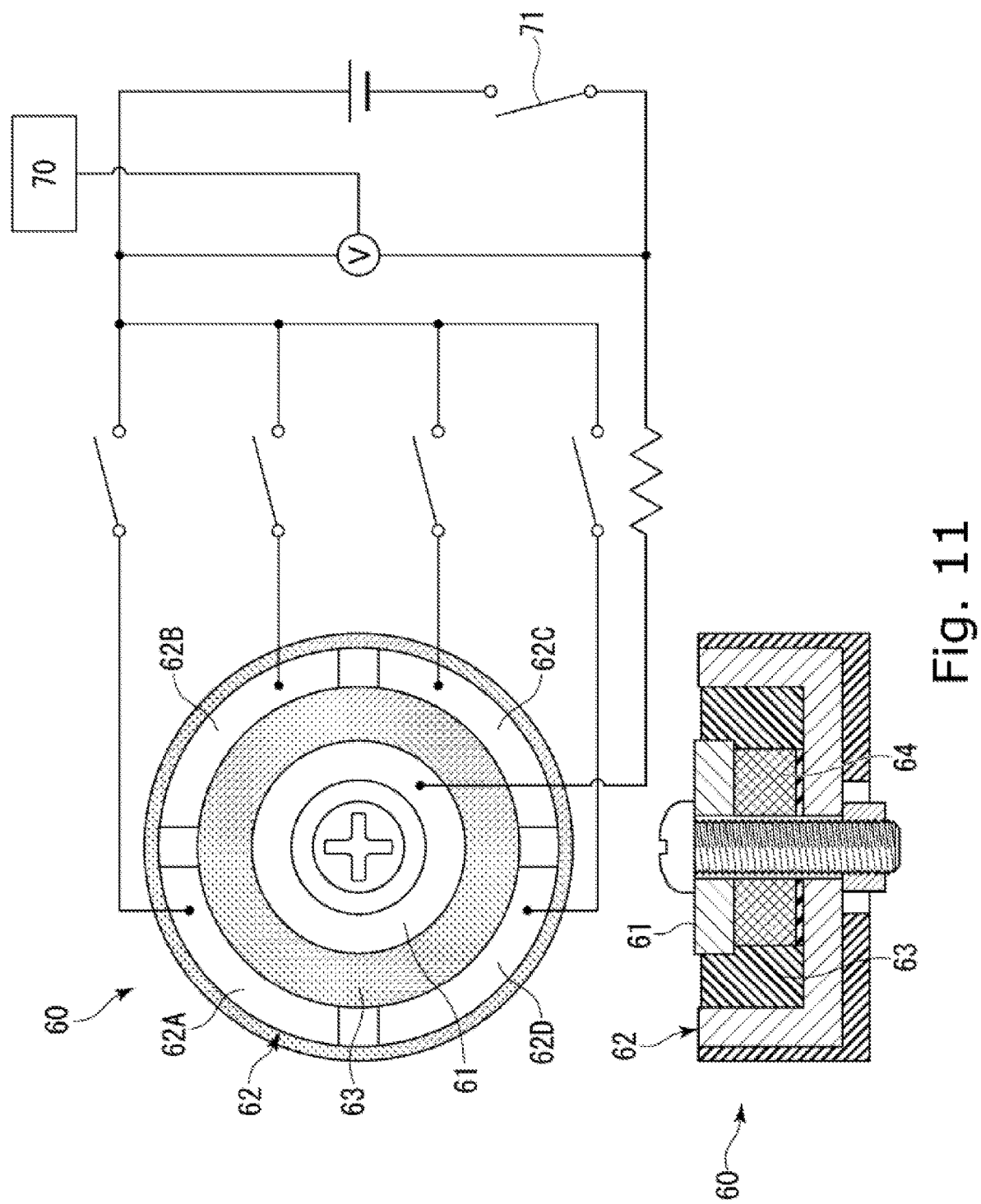
FIG. 11 is used to illustrate a sensor relating to a sixth embodiment of the present invention.

The following describes a sensor relating to a sixth embodiment of the present invention with reference to the drawings. FIG. 11 is used to illustrate the sensor relating to the sixth embodiment. The sensor 60 relating to the sixth embodiment is configured to sense the amount of conductive substance contained in a lubricating oil, similarly to the sensor 30 relating to the above-described second embodiment.

The sensor 60 has a substantially columnar outer shape and includes a plurality of detecting units and a sensing unit 70 configured to output a signal when the detecting units experience a change in electrical resistance and to prevent electrical leakage. More specifically, the sensor 60 includes a center electrode 61, a plurality of outer electrodes 62, an attracting portion 63 disposed between the center electrode 61 and the outer electrode 62, and a magnet 64. The outer electrodes 62 are insulated from each other. Each of the detecting units is constituted by a pair of electrodes and the attracting portion 63 disposed between the paired electrodes. The pair of electrodes includes the center electrode 61 and one of the outer electrodes 62.

In the illustrated embodiment, the sensor 60 includes four outer electrodes 62A, 62B, 62C and 62D, and four detecting units are formed. There are no particular limitations on the number of the outer electrodes 62 and the number of the detecting units. Since the magnet 64 of the sensor 60 forms a magnetic flux line between the paired electrodes, the conductive substance contained in the lubricating oil is attracted by the attracting portion 63. When the conductive substance is gathered in the vicinity of the attracting portion 63 in this manner, the detecting units experience a change in electrical resistance. While no conductive abrasion particles are attracted, the detecting units are equal in electrical resistance.

The center electrode 61 and the outer electrodes 62 are respectively connected to output lines, and each detecting unit is electrically connected to the sensing unit 70 via a corresponding one of the output lines.

In this embodiment, the detecting units are connected in parallel to each other, and voltage is applied between the center electrode 61 and each of the outer electrodes 62 by the same voltage source. The sensing unit 70 outputs a signal when a designated number of the detecting units experience a change in electrical resistance. For example, the sensing unit 70 may be configured to output a signal to a higher-level control device such as a manipulator when two or more of the detecting units experience a drop in electrical resistance, or configured to output a signal when all of the detecting units experience a drop in electrical resistance.

Alternatively, the sensing unit 70 selects a designated one of the detection units in a particular order and outputs a signal when the selected detecting unit experiences a change in electrical resistance. In addition, the sensing unit 70 is configured to output a signal when the detecting units experience a drop in electrical resistance as described above and to, subsequently, turn off the sensing power fed to the sensor 60.

Specifically, the sensing unit 70 is configured to output a signal to put on a failure display when the detecting units experience a drop in electrical resistance as described above and to, subsequently, disconnect a switch 71 in order to turn off the sensing power fed to the sensor 60. In other words, the power is no longer fed once the sensor 60 senses an increase in the amount of iron powder (a drop in resistance of the gap) and thus determines that the speed reducer 2 is malfunctioning.

This can prevent electrical leakage and shock even if the abrasion powder keeps accumulating to cause the sensor 60 to come into contact with the speed reducer 2 or mechanism 1. If the speed reducer 2 is continuously used even after the sensor 60 reports the failure of the speed reducer 2, the iron powder is continuously produced in the speed reducer 2 as the speed reducer 2 operates and the conductive abrasion powder resultantly keeps accumulating on the sensor 60. As the iron powder accumulates, the dimensions of the sensor 60 increase. The abrasion powder resultantly causes the sensor 60 to come into contact with and establish electrical connection with the parts of the mechanism 1, which may disadvantageously result in electrical leakage and shock. The present embodiment can prevent this case.

Figure 12:
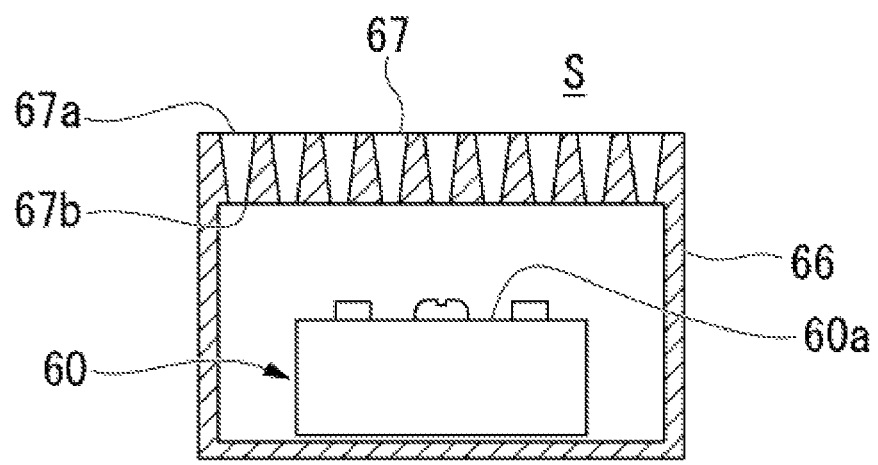
FIG. 12 is used to illustrate a sensor relating to a seventh embodiment of the present invention.

The following describes a sensor relating to a seventh embodiment of the present invention with reference to the drawings. FIG. 12 is used to illustrate the sensor relating to the seventh embodiment. The sensor 60 relating to the seventh embodiment is configured to sense the amount of a conductive substance contained in a lubricating oil, similarly to the sensors 5, 30 and 60 relating to the above-described embodiments. According to the present embodiment, as shown in FIG. 12, a cover 66 is provided to cover the sensor 60 in the space S. The cover 66 houses the sensor 60 therein and has a large number of through holes 67 positioned to face the sensing plane 60a of the sensor 60.

The through holes 67 have a larger diameter at an external opening 67a thereof, which faces the space S external to the cover 66, than at an internal opening 67b thereof, which faces the sensor 60 arranged within the cover 66. When entering the inside of the cover 66 from the space S through the through holes 67, the conductive abrasion powder passes through the through holes 67 having the decreasing diameter and then reaches the sensor 60. The cover 66 is arranged such that the internal opening 67b of the through holes 67 is spaced away from the sensing plane 60a of the sensor 60. The inside of the cover 66 is tightly sealed, except for the through holes 67.

With such configurations, the sensor 60 can be protected by the cover 66 even if the mechanism 1 and the speed reducer 2 violently operate and the lubricant flows violently. This can prevent the conductive abrasion powder from moving back into the external space S after entering the inside of the cover 66. As a result, the sensor 60 can keep the accurate amount of the attracted conductive abrasion powder and reliably predict a failure. In addition, since the conductive abrasion powder is prevented from leaving the space inside the cover 66 after entering the inside of the cover 66, the influence on the mechanism 1 and the speed reducer 2 can be reduced. The cover 66 can have an inner diameter substantially equal to the outer diameter of the sensor 60, when seen in the axial direction of the sensor 60.

Furthermore, according to the present embodiment, the cover 66 can prevent a large amount of abrasion powder from being attracted by the sensor 60 at once during the initial stage of the operation of the speed reducer 2, in which a small amount of abrasion powder is produced. As a result, the sensor 60 can be prevented from malfunctioning. In contrast to the initial stage of the operation of the speed reducer 2, in which a small amount of abrasion powder is produced, a large amount of abrasion powder may be produced immediately before a failure of the speed reducer 2. In this case, the sensor 60 can attract and sense a sufficient amount of abrasion powder that has passed through the through holes 67.

The individual characteristics of the above-described embodiments of the present invention can be combined as appropriate.

In the sensor relating to the present invention, the sensitivity adjusting unit can include a group of insulators having different axial heights with respect to the opening of the outer electrode. In this way, by selecting an appropriate one of the insulators having different axial heights, the sensitivity of the sensor can be set at a predetermined level in accordance with an expected amount of conductive abrasion powder to be generated. Specifically, an insulator having a large axial height is selected when a large amount of conductive abrasion powder is expected to be produced. In this way, a longer distance can be obtained to attract the abrasion powder between the electrodes to set the sensitivity of the sensor at a predetermined level. Alternatively, an insulator having a small axial height or being flush with the electrode is selected when a small amount of conductive abrasion powder is expected to be produced. In this way, a shorter distance can be obtained to attract the abrasion powder between the electrodes to set the sensitivity of the sensor at a predetermined level.

In the sensor relating to the present invention, the sensitivity adjusting unit can include a group of insulators having different radial thicknesses, which are adjacent to the opening of the outer electrode, with respect to the outer diameter of the inner electrode and a corresponding group of outer electrodes corresponding to the outer diameters of the individual insulators. In this way, by selecting an appropriate one of the insulators having different radial thicknesses, the sensitivity of the sensor can be set at a predetermined level in accordance with an expected amount of conductive abrasion powder to be produced. Specifically, an insulator having a large radial thickness is selected when a large amount of conductive abrasion powder is expected to be produced. In this way, a longer distance can be obtained to attract the abrasion powder between the electrodes to set the sensitivity of the sensor at a predetermined level. Alternatively, an insulator having a small radial thickness is selected when a small amount of conductive abrasion powder is expected to be produced. In this way, a shorter distance can be obtained to attract the abrasion powder between the electrodes to set the sensitivity of the sensor at a predetermined level.

In the sensor relating to the present invention, the outer electrode can have an open end that is flush with the inner electrode.

In the sensor relating to the present invention, the sensitivity adjusting unit can include another magnet provided in addition to the above-mentioned magnet. In this case, the other magnet can be selected from a group of magnets capable of attracting different amounts of abrasion powder, or the other magnet can be omitted. In this way, depending on the expected amount of conductive abrasion powder to be produced, another magnet is employed to attract the abrasion powder, which can reduce the amount of the abrasion powder to be attracted between the electrodes. Thus, the sensitivity of the sensor can be set at a predetermined level. Specifically, when a large amount of conductive abrasion powder is expected to be produced, another magnet having strong magnetic force or a large size is selected, which reduces the amount of the abrasion powder to be attracted between the electrodes. Thus, the sensitivity of the sensor can be set at a predetermined level. Alternatively, when a small amount of conductive abrasion powder is expected to be produced, another magnet having weak magnetic force or a small size is selected, or another magnet is not provided, which allows a predetermined amount of abrasion powder to be attracted between the electrodes. Thus, the sensitivity of the sensor can be set at a predetermined level.

In the sensor relating to the present invention, the sensitivity adjusting unit can include a surface treatment layer of the outer electrode and a surface treatment layer of the inner electrode. Here, sludge may possibly reduce the amount of abrasion powder to be attracted. The sludge may adhere to the attraction surface of the electrodes and reduce the amount of abrasion powder to be attracted between the electrodes, which does not allow the sensor to provide required sensitivity. The above configuration of the present invention can prevent this problem. Specifically, the surface treatment layers may be only required to have electrical conductivity, smoothness, slipperiness, and low adhesiveness.

In the sensor relating to the present invention, the sensitivity adjusting unit can be a cover that at least covers a pair of electrodes and the attracting portion disposed between the paired electrodes.

What is claimed is:

1. A sensor comprising: a first electrode; a second electrode; a magnet configured to gather conductive particles between the first electrode and the second electrode; an attracting portion arranged between the first electrode and the second electrode; a sensing unit configured to sense a change in electrical resistance between the first electrode and the second electrode; and a short circuit preventing portion configured to prevent a short circuit between the first electrode and the second electrode, wherein the short circuit preventing portion and the attracting portion form a one-piece structure.

2. The sensor of claim 1, wherein the short circuit preventing portion is a protrusion having an insulation property, and the protrusion is provided on at least one of the first electrode and the second electrode.

3. The sensor of claim 1, wherein the short circuit preventing portion is a protrusion provided on the attracting portion.

4. The sensor of claim 1, wherein the short circuit preventing portion has an insulation property.

5. The sensor of claim 1, wherein the short circuit preventing portion is a wire extending along a direction intersecting with a direction in which the first electrode and the second electrode face each other.

* * * * *